(12) United States Patent
Mason et al.

(10) Patent No.: US 10,017,523 B2
(45) Date of Patent: Jul. 10, 2018

(54) NAMPT INHIBITORS AND METHODS

(71) Applicant: Genzyme Corporation, Cambridge, MA (US)

(72) Inventors: Paul Mason, Natick, MA (US); Kara Carter, Cambridge, MA (US); Alexandra Joseph, Lexington, MA (US); Yiding Hu, Lexington, MA (US); Jill Gregory, Acton, MA (US); Zhong Zhao, Wayland, MA (US); Christopher Yee, Needham, MA (US); Mohamud Mohamud, Minnetonka, MN (US); Yibin Xiang, Dracut, MA (US); Sanjay Danthi, Roxbury, MA (US); Yinyin Huang, Chestnut Hill, MA (US); Andrew Papoulis, Canton, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 15/312,482

(22) PCT Filed: May 22, 2015

(86) PCT No.: PCT/US2015/032170
§ 371 (c)(1),
(2) Date: Nov. 18, 2016

(87) PCT Pub. No.: WO2015/179759
PCT Pub. Date: Nov. 26, 2015

(65) Prior Publication Data
US 2017/0107231 A1 Apr. 20, 2017

Related U.S. Application Data

(60) Provisional application No. 62/001,905, filed on May 22, 2014.

(51) Int. Cl.
| | | |
|---|---|---|
| *C07D 498/10* | (2006.01) | |
| *C07D 491/107* | (2006.01) | |
| *C07D 491/20* | (2006.01) | |
| *C12N 5/0781* | (2010.01) | |

(Continued)

(52) U.S. Cl.
CPC ....... *C07D 498/10* (2013.01); *C07D 491/107* (2013.01); *C07D 491/20* (2013.01); *C12N 5/0635* (2013.01); *G01N 33/5008* (2013.01); *G01N 33/60* (2013.01)

(58) Field of Classification Search
CPC . C07D 498/10; C07D 491/107; C07D 491/20
See application file for complete search history.

(56) References Cited

U.S. PATENT DOCUMENTS

2007/0117823 A1  5/2007  Antel et al.

FOREIGN PATENT DOCUMENTS

| WO | WO 2002/000196 | 1/2002 |
| WO | WO 2007/088462 | 8/2007 |
| WO | WO 2012/077655 | 6/2012 |

OTHER PUBLICATIONS

International Search Report and Written Opinion; PCT/US2015/032170; dated Jul. 21, 2015; 10 pages.

(Continued)

*Primary Examiner* — Rebecca L Anderson
(74) *Attorney, Agent, or Firm* — Fish & Richardson P.C.

(57) ABSTRACT

The invention features compounds of Formula (I), Formula (I)-A and Formula (I)-B as disclosed herein, as well as methods of synthesis, therapy, diagnostics, and assays.

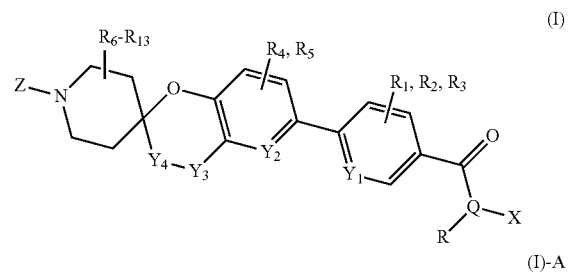

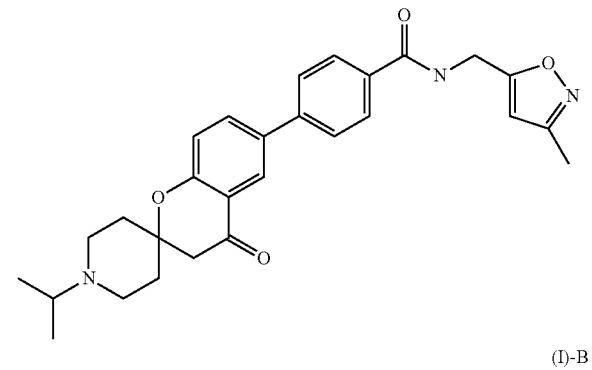

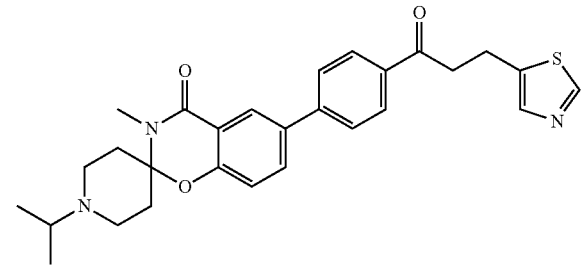

38 Claims, 7 Drawing Sheets

(51) Int. Cl.
    *G01N 33/50*    (2006.01)
    *G01N 33/60*    (2006.01)

(56) References Cited

OTHER PUBLICATIONS

Galli et al., "Medicinal Chemistry of Nicotinamide Phosphoribosetransferase (NAMPT) Inhibitors", J. Med. Chem. 2013 (56(16), pp. 6279-6296.

Zhang RY, et al.; "A fluorometric assay for high-throughput screening targeting nicotinamide phosphoribosyltransferase", Anal. Biochem. May 1, 2011;412(1):18-25.

International Preliminary Report on Patentability; PCT/US2015/032170; dated Nov. 22, 2016; 8 pages.

NAMPT INHIBITORS AND METHODS

CROSS-REFERENCE TO RELATED APPLICATIONS

This application is a U.S. National Phase application under 35 U.S.C. § 371 of International Patent Application No. PCT/US2015/032170 filed May 22, 2015, which claims priority under 35 U.S.C. § 119(e) to U.S. Provisional Application No. 62/001,905 filed May 22, 2014, the disclosure of which is incorporated herein in its entirety.

TECHNICAL FIELD

This invention relates generally to therapeutics and treatments for various disorders, including, without limitation, oncological disorders, immunological disorders, viral infections and disorders related to nicotinamide phoshophoribosyltransferase (NAMPT).

BACKGROUND

Two NAMPT inhibitors (FK866 and CHS828) have entered clinical trials. See generally, Galli et al., "Medicinal Chemistry of Nicotinamide Phosphoribosetransferase (NAMPT) Inhibitors", J. Med. Chem. 2013 (56(16), pp 6279-6296.

SUMMARY

The present invention provides, inter alia, compounds of Formula (I):

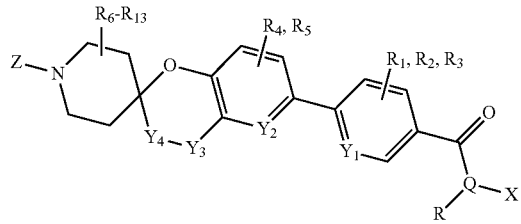

Formula (I)

or a pharmaceutically acceptable salt thereof, wherein:
$Y_1$ is —$CR_{14}$— or N,
$Y_2$ is $CR_{15}$ or N,
$Y_3$ is —C(O)—,
$Y_4$ is —$CH_2$, or —N($R_{16}$)—,
or $Y_3$ and $Y_4$ together are —C($R_{17}$)=C($R_{18}$)—,
X is aryl, heteroaryl, arylalkyl, heteroarylalkyl, or amide,
Z is $C_2$ or greater alkyl or alkoxylalkyl,
R is H or $C_1$-$C_6$ alkyl,
$R_1$-$R_{18}$ are independently —H or $C_1$-$C_6$ alkyl, and
Q is C or N; provided that when Q is N and R is H, X is not

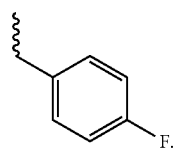

Preferably, X is phenyl or substituted phenyl, e.g., fluorophenyl; R is H; X is pyridinyl or substituted pyridinyl, e.g., fluoropyridinyl or methylpyridinyl. Also preferably, $Y_1$ is C; $Y_1$ is N; $Y_2$ is C $Y_2$ is N; $Y_3$ is —C(O)=; $Y_4$ is —C(H)=. Also preferably Z is $C_2$-$C_4$ alkyl or propyl, e.g., isopropyl. Also preferably, Z is alkoxyalkyl or cyclobutylmethyl. Also preferably, $R_{17}$ and $R_{18}$, and most preferably $R_1$-$R_{16}$ as well, are —H.

In other preferred embodiments, the compound has one of the following Formulas (I)-A or (I)-B:

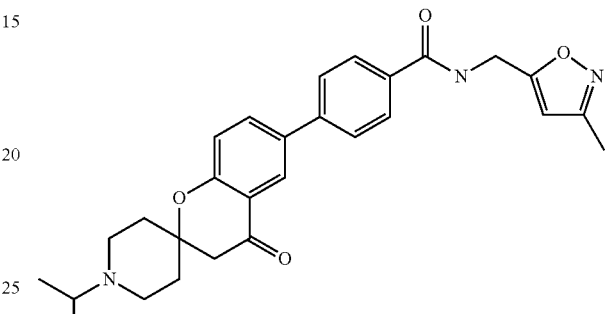

Formula (I)-A

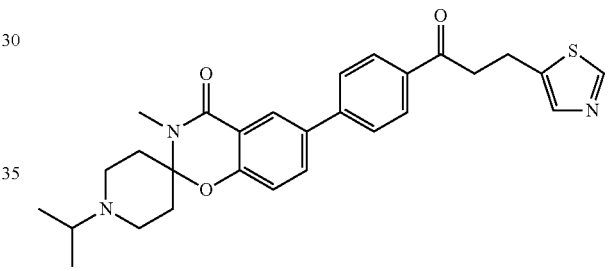

Formula (I)-B

The above compounds may be used to inhibit activated and/or proliferating B cells for therapeutic modulation of immunological disease by administering a composition comprising the compound to a patient in need thereof. For example, the immunological disease may be lupus, rheumatoid arthritis, scleroderma, psoriasis, Sjogren's syndrome, type I diabetes or multiple sclerosis. The compounds may be used for inducing, modulating or maintaining immunosuppression for transplant by administering a composition comprising the compound to a patient in need thereof. Other medical uses include: suppressing or modulating an immune response to a therapeutic biologic such as a recombinant protein, a nucleic acid, an antibody or a peptide; inhibiting tumor cell growth, particularly for NAPRT deficient tumor cells; treating leukemia (e.g., acute lymphocytic leukemia) and lymphoma; treating a viral infection such as, influenza, respiratory syncytial virus (RSV), herpes simplex virus (HSV), hepatitis C virus (HCV), hepatitis B virus (HBV), human papilloma virus (HPV), human immunodeficiency virus (HIV), human cytomegalovirus (CMV), Ebolavirus (EBOV), and Epstein-Barr virus (EBV). Other uses for the compounds include inhibiting differentiation of B cells (e.g., in vivo or in vitro) into plasma cells, by contacting the B cells with the compound. The presence of a compound according to the invention in a sample (e.g., a sample suspected of containing the compound) may be detected by contacting the sample with a binding agent that binds to the compound and detecting binding of the agent to the compound. The compound may further comprise a detectable label, e.g., to facilitate such detection.

In another aspect, the invention features synthesizing the compound by reacting a benzoic acid derivative with carbonyl diimidazole and a methanamine derivative.

These compounds have applications as therapeutics for multiple immunological and oncological diseases including, but not limited to, lupus, rheumatoid arthritis, Sjogren's syndrome, type I diabetes, multiple sclerosis, transplant induction and maintenance, scleroderma, acute lymphocytic leukemia, and cancer, particularly NAPRT-deficient solid or liquid tumors. In addition, they are therapeutics for NAD-requiring viral infections including, but not limited to, influenza, RSV, HSV, HCV, HBV, HPV, HIV, CMV, EBOV, and EBV.

The present invention also provides methods of treating the above conditions by administering to a patient a therapeutically effective amount of such a compound or a pharmaceutically acceptable salt thereof. The present invention also provides use or manufacture of the compound, or a pharmaceutically acceptable salt thereof, for use in therapy. The present invention also provides such a compound, or a pharmaceutically acceptable salt thereof, for use in the treatment of a disease referenced herein.

While not wishing to bind ourselves to a specific mechanism of action, the compounds selectively inhibit human primary B cells while sparing T cells. In general, the compounds target NAMPT and inhibit primary human B cell activation and proliferation while selectively sparing primary human T cells, and they are useful for treating B cell-mediated and proliferative disorders including various immune-mediated diseases as well as cancer, in particular B-cell malignancies, NAPRT-deficient solid or liquid tumors and NAD-requiring viral infections including, but not limited to, influenza, RSV, HSV, HCV, HBV, HPV, HIV, CMV, EBOV, and EBV.

The details of one or more embodiments of the invention are set forth in the accompanying drawings and the description below. Other features, objects, and advantages of the invention will be apparent from the description and drawings, and from the claims.

DETAILED DESCRIPTION

I. Compounds

Figure 1:
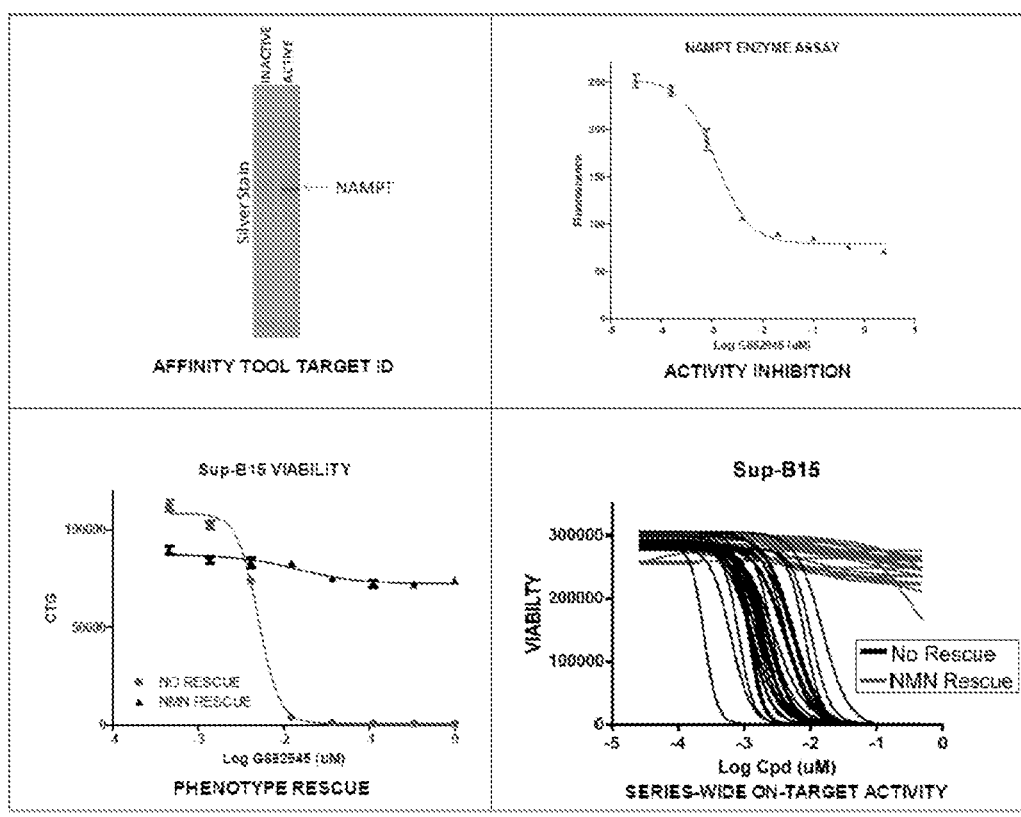
FIG. 1 are graphs demonstrating the mechanism of action of the compounds described herein.

The present disclosure relates, inter alia, to a compound of Formula (I), Formula (I)-A and Formula (I)-B, above.

General Definitions

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

For the terms "e.g." and "such as," and grammatical equivalents thereof, the phrase "and without limitation" is understood to follow unless explicitly stated otherwise. As used herein, the singular forms "a," "an," and "the" include plural referents unless the context clearly dictates otherwise. As used herein, the term "about" means "approximately" (e.g., plus or minus approximately 10% of the indicated value).

As used herein, the phrase "optionally substituted" means unsubstituted or substituted. As used herein, the term "substituted" means that a hydrogen atom is removed and replaced by a substituent. In general all moieties may be substituted unless otherwise indicated. It is to be understood that substitution at a given atom is limited by valency. Throughout the definitions, the term "$C_{n-m}$" indicates a range which includes the endpoints, wherein n and m are integers and indicate the number of carbons. Examples include $C_{1-4}$, $C_{1-6}$, and the like.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, and propoxy (e.g., n-propoxy and isopropoxy). In some embodiments, the alkyl group has 1 to 3 carbon atoms.

As used herein, "$C_{n-m}$ alkenyl" refers to an alkyl group having one or more double carbon-carbon bonds and having n to m carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6 or 1 to 4 carbon atoms.

As used herein, the term "di-$C_{n-m}$-alkylamino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "$C_{n-m}$ alkylthio" refers to a group of formula —S-alkyl, wherein the alkyl group has n to m carbon atoms. In some embodiments, the alkyl group has 1 to 6 or 1 to 4 carbon atoms.

As used herein, the term "amino" refers to a group of formula —NH$_2$.

As used herein, the term "aryl", employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "carbonyl", employed alone or in combination with other terms, refers to a —C(O)— group.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-7}$ cycloalkyl, which is monocyclic or bicyclic. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, the cycloalkyl group is cyclopropyl, cyclobutyl, cyclopentyl, or cyclohexyl.

As used herein, "$C_{n-m}$ haloalkoxy" refers to a group of formula —O-haloalkyl having n to m carbon atoms. An example haloalkoxy group is OCF$_3$. An additional example haloalkoxy group is OCHF$_2$. In some embodiments, the haloalkoxy group is fluorinated only. In some embodiments, the alkyl group has 1 to 6 or 1 to 4 carbon atoms.

As used herein, the term "halo" refers to a halogen atom selected from F, Cl, I or Br. In some embodiments, "halo" refers to a halogen atom selected from F, Cl, or Br. In some embodiments, exemplary halo groups are F.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is 5- to 10-membered $C_{1-9}$ heteroaryl, which is monocyclic or bicyclic and which has 1, 2, 3, or 4 heteroatom ring members independently selected from nitrogen, sulfur and oxygen. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1, 2-b]thiazole, purine, triazine or the like.

A 5-membered heteroaryl is a heteroaryl group having five ring atoms comprising carbon and one or more (e.g., 1, 2, or 3) ring atoms independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1, 2, 3-triazolyl, tetrazolyl, 1, 2, 3-thiadiazolyl, 1, 2, 3-oxadiazolyl, 1, 2, 4-triazolyl, 1, 2, 4-thiadiazolyl, 1, 2, 4-oxadiazolyl, 1, 3, 4-triazolyl, 1, 3, 4-thiadiazolyl, and 1, 3, 4-oxadiazolyl A 6-membered heteroaryl is a heteroaryl group having six ring atoms wherein one or more (e.g., 1, 2, or 3) ring atoms are nitrogen. Exemplary six-membered ring heteroaryls are pyridyl, pyrazinyl, pyrimidinyl, triazinyl and pyridazinyl As used herein, the term "heterocycloalkyl", employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl group contains more than one heteroatom, the heteroatoms may be the same or different. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1, 2, 3, 4-tetrahydro-quinoline, dihydrobenzofuran and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is 5- to 10-membered $C_{2-9}$ heterocycloalkyl, which is monocyclic or bicyclic and which has 1, 2, 3, or 4 heteroatom ring members independently selected from nitrogen, sulfur and oxygen. Examples of heterocycloalkyl groups include 1, 2, 3, 4-tetrahydroquinoline, dihydrobenzofuran, azetidine, azepane, pyrrolidine, piperidine, piperazine, morpholine, thiomorpholine, and pyran.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as D-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1, 2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, $^1$H- and $^3$H-imidazole, $^1$H-, $^2$H- and $^4$H-1, 2, 4-triazole, $^1$H- and $^2$H-isoindole, and $^1$H- and $^2$H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in Remington's Pharmaceutical Sciences, 17th Ed., (Mack Publishing Company, Easton, 1985), p. 1418, Berge et al., J. Pharm. Sci., 1977, 66(1), 1-19, and in Stahl et al., Handbook of Pharmaceutical Salts: Properties, Selection, and Use, (Wiley, 2002). In some embodiments, the compounds described herein include the N-oxide forms.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DIAD (N, N'-diisopropyl azidodicarboxylate); DIPEA (N, N-diisopropylethylamine); DMF (N, N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); mg (microgram(s)); μL (microliter(s)); μM (micromolar); wt % (weight percent).

II. Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, Protective Groups in Organic Synthesis, 4$^{th}$ Ed., Wiley & Sons, Inc., New York (2006), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety) and normal phase silica chromatography.

III. Specific Examples

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1: Methods of Synthesis

Example 1-1: 4-(1'-isopropyl-4-oxospiro[chroman-2,4'-piperidin]-6-yl)-N-((3-methylisoxazol-5-yl)methyl)benzamide

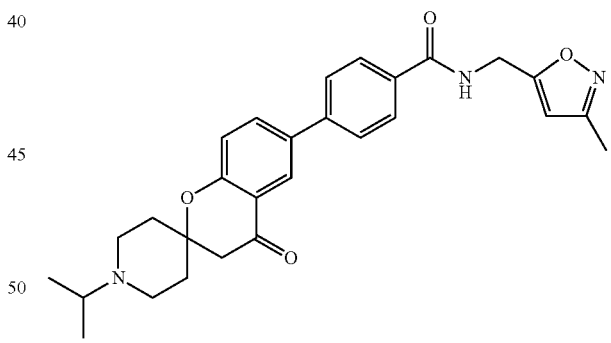

To a solution of 4-(1'-isopropyl-4-oxospiro[chroman-2,4'-piperidin]-6-yl)benzoic acid (100 mg) in DMF (2 mL) were added 1,1'-carbonyldiimidazole (64 mg, 1.5 eq) and (3-methylisoxazol-5-yl)methanamine (44 mg, 1.5 eq). The mixture was stirred overnight at RT. The mixture was then diluted with AcOEt and quenched with a saturated solution of NaHCO$_3$. The organic phase was washed with brine and dried over MgSO$_4$. After filtration, the residue was evaporated under vacuum to give a crude yellow foam. This material was purified on silicagel cartridge using a gradient of solvent 0-20% MeOH in DCM. 4-(1'-isopropyl-4-oxospiro[chroman-2,4'-piperidin]-6-yl)-N-((3-methylisoxazol-5-yl)methyl)benzamide was obtained as a yellow foam (71.5 mg, 79%), LCMS RT=3.34 min.

Example 1-2: N-((5-fluoropyridin-3-yl)methyl)-4-(1'-isopropyl-3-methyl-4-oxo-3,4-dihydrospiro[benzo[e][1,3]oxazine-2,4'-piperidin]-6-yl)benzamide

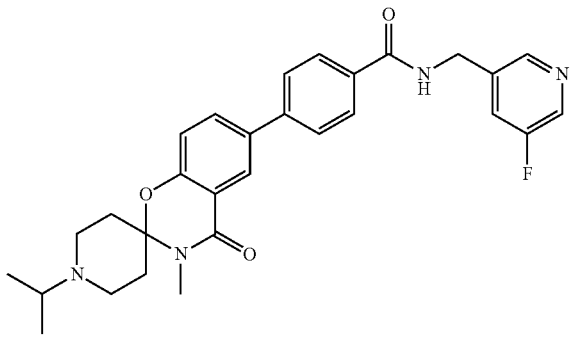 [SMILES: CC(C)N1CCC2(CC1)Oc1ccc(-c3ccc(C(=O)NCc4cncc(F)c4)cc3)cc1C(=O)N2C]

4-(1'-isopropyl-2-methyl-1-oxo-2,4-dihydro-1H-spiro[isoquinoline-3,4'-piperidin]-7-yl)benzoic acid-lithium chloride salt (100 mg, 0.263 mmoles) and HATU (100 mg, 0.263 mmoles) were combined in 2 mL DMF. DIEA (0.09 mL) was added to the solution. After the mixture was stirred for 5 minutes at RT, (5-fluoropyridin-3-yl)methanamine (0.289 mmoles) was added. The mixture was stirred at RT overnight before it was quenched using a saturated solution of NaHCO$_3$ and diluted with AcOEt. After the aqueous phase was extracted with AcOEt, the combined organic phases were dried using Na$_2$SO$_4$, filtered and concentrated under vacuum. The residue was purified on flash chromatography using a gradient 0-20% MeOH in DCM. The reaction yielded 110 mg of N-((5-fluoropyridin-3-yl)methyl)-4-(1'-isopropyl-3-methyl-4-oxo-3,4-dihydrospiro[benzo[e][1,3]oxazine-2,4'-piperidin]-6-yl)benzamide.

Example 1-3: 3-fluoro-4-(1'-isopropyl-4-oxospiro[chroman-2,4'-piperidin]-6-yl)-N-((6-methylpyridin-3-yl)methyl)benzamide

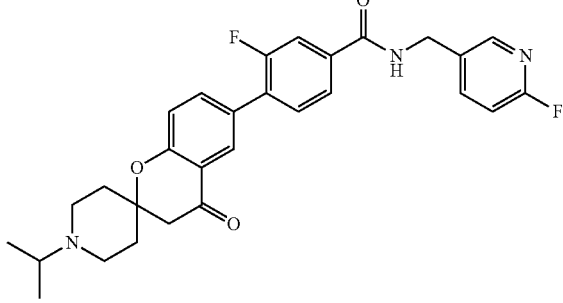

3-fluoro-4-(1'-isopropyl-4-oxospiro[chroman-2,4'-piperidin]-6-yl)-N-((6-methylpyridin-3-yl)methyl)benzamide was obtained using the same method described for Example 1-1. (LCMS RT=2.65 min, MH+251.4, m=30 mg, yield=21%).

Example 1-4: 6-(4-oxo-1'-propylspiro[chroman-2,4'-piperidin]-6-yl)-N-(thiazol-5-ylmethyl)nicotinamide

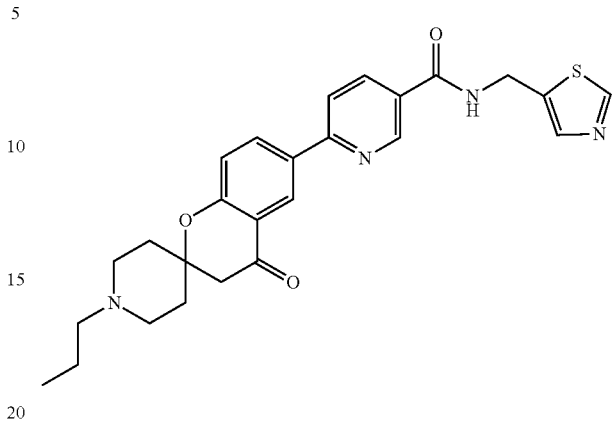

6-(4-oxospiro[chroman-2,4'-piperidin]-6-yl)-N-(thiazol-5-ylmethyl)nicotinamide (150 mg, 0.345 mmoles) was combined with cesium carbonate (135 mg, 0.41 mmoles) and 1-idopropane (58.6 mg, 0.345 mmoles) in 3 mL of DMF. The reaction mixture was stirred at RT for 72 hours. Then the mixture was quenched with water and diluted with AcOEt. After extraction using AcOEt, the combined organic phases were washed with brine and dried using MgSO$_4$. After filtration, the solvent was removed in vacuo to get a brown semi-solid. The crude material was purified on silicagel cartridge using a gradient 0-15% MeOH in DCM. The desired fractions were combined and evaporated to get a tan solid (LCMS RT=3.07 min, 49 mg, 29%).

Example 1-5: 6-(1'-butyl-4-oxospiro[chroman-2,4'-piperidin]-6-yl)-N-(thiazol-5-ylmethyl)nicotinamide

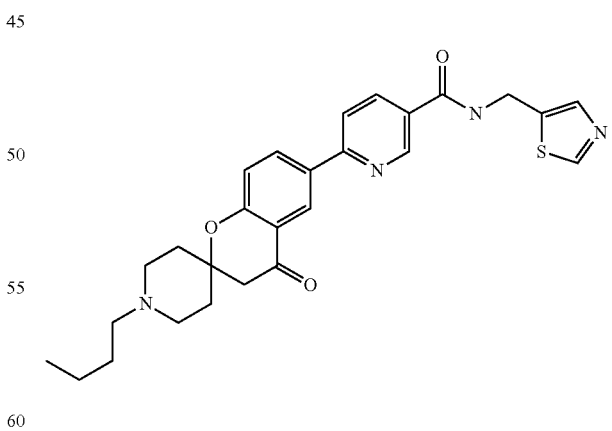

6-(1'-butyl-4-oxospiro[chroman-2,4'-piperidin]-6-yl)-N-(thiazol-5-ylmethyl)nicotinamide was obtained using the same method described for Example 1-4. (LCMS RT=3.25 min, MH+490.8, m=78 mg as a tan solid, yield=48.4%).

Example: 1-6: N-((3-methylisoxazol-5-yl)methyl)-4-(4-oxo-1'-propylspiro[chroman-2,4'-piperidin]-6-yl)benzamide

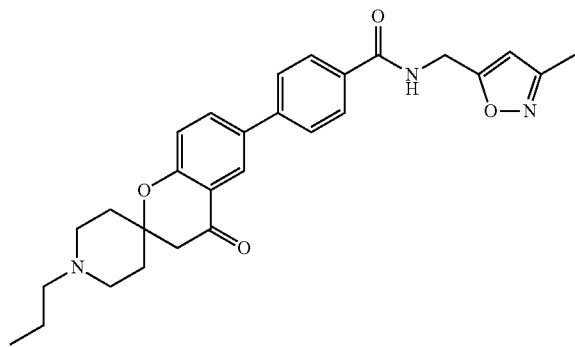 [SMILES: CCCN1CCC2(CC1)CC(=O)c1cc(-c3ccc(C(=O)NCc4cc(C)no4)cc3)ccc1O2]

N-((3-methylisoxazol-5-yl)methyl)-4-(4-oxo-1'-propyl-spiro[chroman-2,4'-piperidin]-6-yl)benzamide was obtained using the same method described for Example 1-1. (LCMS RT=3.27 min, m=11 mg, yield=12%).

Example 1-7: N((3-methylisoxazol-5-yl)methyl)-6-(1'-propylspiro[chromene-2,4'-piperidin]6- yl)nicotinamide

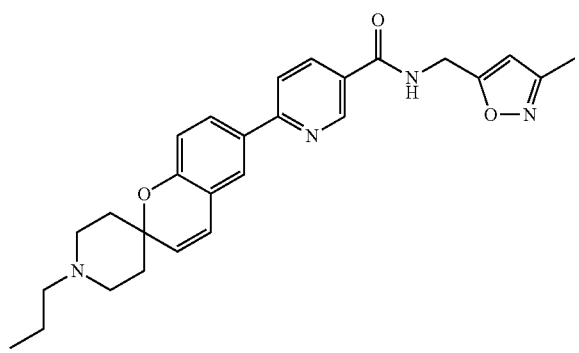 [SMILES: CCCN1CCC2(C=Cc3cc(-c4ccc(C(=O)NCc5cc(C)no5)cn4)ccc3O2)CC1]

N-((3-methylisoxazol-5-yl)methyl)-6-(4-oxo-1'-propyl-spiro[chroman-2,4'-piperidin]-6-yl)nicotinamide (66 mg, 0.14 mmoles) was dissolved in 1.5 mL of MeOH. Sodium borohydride (33 mg, 0.87 mmoles) was added to the reaction mixture in one portion. Degassing happened for several minutes then the yellowish mixture became colorless. After 3 hours at RT, the reaction is completed. The mixture was quenched with water and diluted with AcOEt. The aqueous phase was extracted with AcOEt and the combined organic phases were washed with brine twice. The organic phase was then dried using $MgSO_4$ and concentrated under vacuum.

To the crude material was then added 8 mL of water and 2 mL of concentrated $H_2SO_4$. The mixture was stirred vigorously and heated at 80° C. After 48 hours at this temperature, the mixture was diluted with water, basified using solid $Na_2CO_3$. The aqueous phase was extracted with AcOEt and the combined organic phases were washed with brine twice. After filtration and evaporation, the crude residue was purified on silica gel cartridge using 20% MeOH in DCM. The desired fractions were combined and concentrated under vacuum. N-((3-methylisoxazol-5-yl)methyl)-6-(1'-propylspiro[chromene-2,4'-piperidin]-6-yl)nicotinamide was obtained as a white solid (21 mg, 33.3%, LCMS RT=3.30 min, MH+459.3).

Example 1-8: 6-(1'-(3-methoxypropyl)spiro[chromene-2,4'-piperidin]-6-yl)-N-(thiazol-5-ylmethyl)nicotinamide

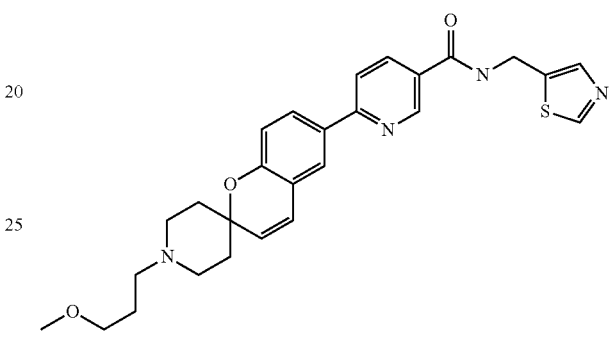

6-(1'-(3-methoxypropyl)spiro[chromene-2,4'-piperidin]-6-yl)-N-(thiazol-5-ylmethyl)nicotinamide was obtained using the same method described for Example 1-7.

Example 1-9: 6-(1'-isopropyl-3-methyl-4-oxo-3,4-dihydrospiro[benzo[e][1,3]oxazine-2,4'-piperidin]-6-yl)-N-((1-methyl-1H-pyrazol-4-yl)methyl)nicotinamide

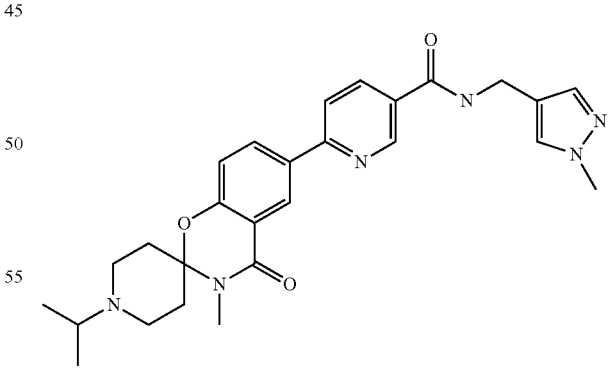

6-(1'-isopropyl-3-methyl-4-oxo-3,4-dihydrospiro[benzo[e][1,3]oxazine-2,4'-piperidin]-6-yl)-N-((1-methyl-1H-pyrazol-4-yl)methyl)nicotinamide was obtained using the same method described for Example 1-2.

Example 1-10: 6-(1'-isopropyl-3-methyl-4-oxo-3,4 dihydrospiro[benzo[e][1,3]oxazine-2,4'-piperidin]-6-yl)-N-(thiazol-5-ylmethyl)nicotinamide

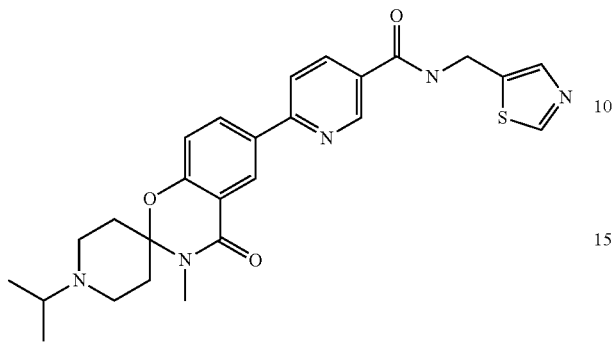

6-(1'-isopropyl-3-methyl-4-oxo-3,4 dihydrospiro[benzo[e][1,3]oxazine-2,4'-piperidin]-6-yl)-N-(thiazol-5-ylmethyl) nicotinamide was obtained using the same method described for Example 1-2.

Example 1-11: 4-(1'-isopropyl-4-oxospiro[chroman-2,4'-piperidin]-6-yl)-N-((5-methylisoxazol-3-yl)methyl)benzamide

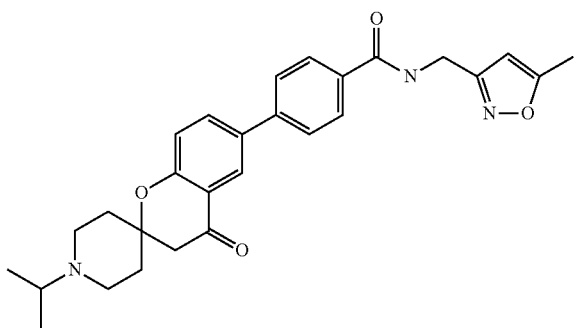 [SMILES: Cc1cc(CNC(=O)c2ccc(-c3ccc4c(c3)C(=O)CC3(CCN(C(C)C)CC3)O4)cc2)no1]

4-(1'-isopropyl-4-oxospiro[chroman-2,4'-piperidin]-6-yl)-N-((5-methylisoxazol-3-yl)methyl)benzamide was obtained using the same method described for Example 1-1. (LCMS RT=3.35 min, m=49.7 mg, yield=39%).

Example 1-12: 6-(1'-isopropyl-3-methyl-4-oxo-3,4-dihydrospiro[benzo[1,3]oxazine-2,4'-piperidin]-6-yl)-N-((3-methylisoxazol-5-yl)methyl)nicotinamide

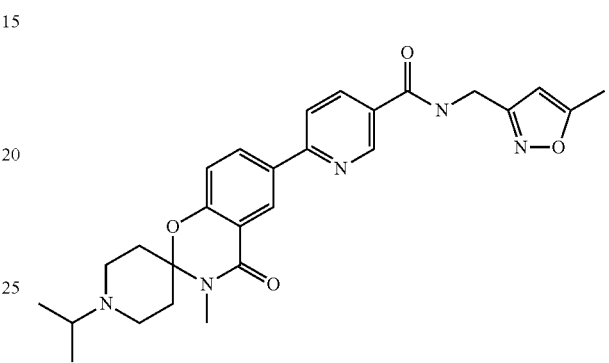

6-(1'-isopropyl-3-methyl-4-oxo-3,4-dihydrospiro[benzo[e][1,3]oxazine-2,4'-piperidin]-6-yl)-N-((3-methylisoxazol-5-yl)methyl)nicotinamide was obtained using the same method described for Example 1-2.

Example 1-13: Additional Compounds of Formula (I)

Additional compounds of Formula (I) were synthesized according to the methods similar to those described above, which are readily apparent to one of skill in the art. These compounds are summarized in Table 1 below.

TABLE 1

Additional Compounds of Formula (I)

| Structure | Compound Name |
|---|---|
| 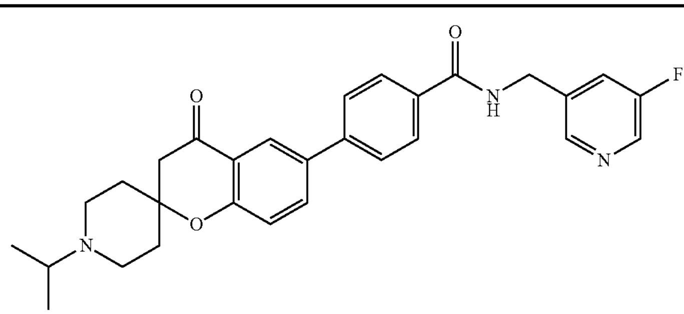 | N-((5-fluoropyridin-3-yl)methyl)-4-(1'-isopropyl-4-oxospiro[chroman-2,4'-piperidin]-6-yl)benzamide |

TABLE 1-continued

Additional Compounds of Formula (I)

| Structure | Compound Name |
|---|---|
| 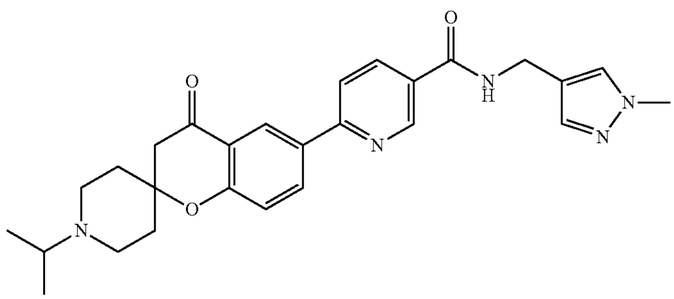 [SMILES: CC(C)N1CCC2(CC1)CC(=O)c1cc(-c3ccc(C(=O)NCc4cnn(C)c4)cn3)ccc1O2] | 6-(1'-isopropyl-4-oxospiro[chroman-2,4'-piperidin]-6-yl)-N-((1-methyl-1H-pyrazol-4-yl)methyl)nicotinamide |
| 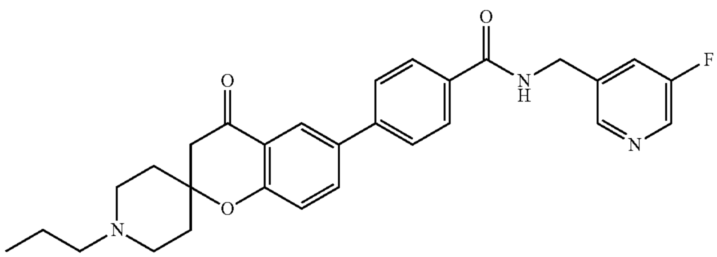 [SMILES: CCCN1CCC2(CC1)CC(=O)c1cc(-c3ccc(C(=O)NCc4cncc(F)c4)cc3)ccc1O2] | N-((5-fluoropyridin-3-yl)methyl)-4-(4-oxo-1'-propylspiro[chroman-2,4'-piperidin]-6-yl)benzamide |
| 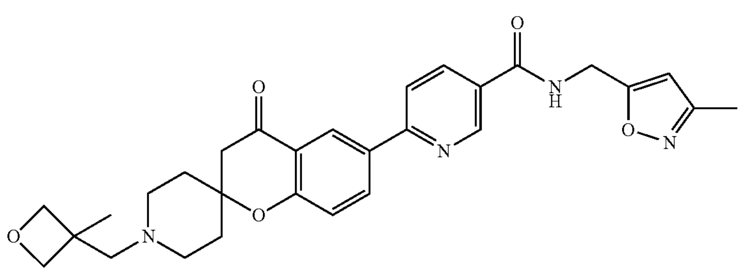 [SMILES: Cc1cc(CNC(=O)c2ccc(-c3ccc4c(c3)C(=O)CC3(CCN(CC5(C)COC5)CC3)O4)nc2)on1] | N-((3-methylisoxazol-5-yl)methyl)-6-(1'-((3-methyloxetan-3-yl)methyl)-4-oxospiro[chroman-2,4'-piperidin]-6-yl)nicotinamide |
| 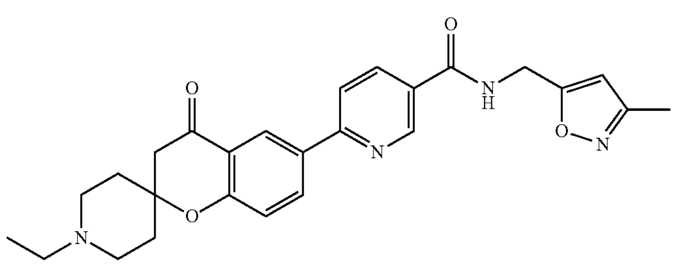 [SMILES: CCN1CCC2(CC1)CC(=O)c1cc(-c3ccc(C(=O)NCc4cc(C)no4)cn3)ccc1O2] | 6-(1'-ethyl-4-oxospiro[chroman-2,4'-piperidin]-6-yl)-N-((3-methylisoxazol-5-yl)methyl)nicotinamide |
| 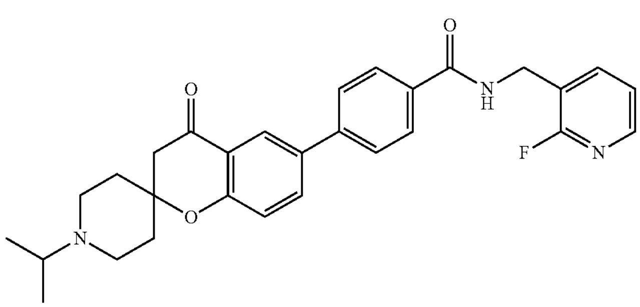 [SMILES: CC(C)N1CCC2(CC1)CC(=O)c1cc(-c3ccc(C(=O)NCc4cccnc4F)cc3)ccc1O2] | N-((2-fluoropyridin-3-yl)methyl)-4-(1'-isopropyl-4-oxospiro[chroman-2,4'-piperidin]-6-yl)benzamide |

TABLE 1-continued

Additional Compounds of Formula (I)

| Structure | Compound Name |
|---|---|
| 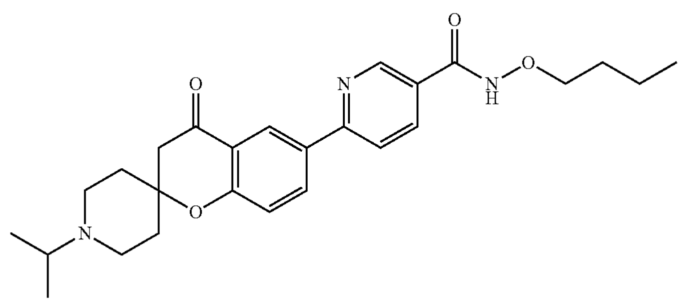 [SMILES: CCCCONC(=O)c1ccc(-c2ccc3c(c2)C(=O)CC2(CCN(C(C)C)CC2)O3)nc1] | N-butoxy-6-(1'-isopropyl-4-oxospiro[chroman-2,4'-piperidin]-6-yl)nicotinamide |
| 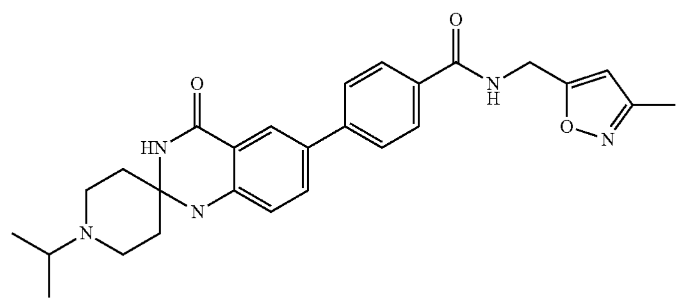 [SMILES: Cc1cc(CNC(=O)c2ccc(-c3ccc4c(c3)C(=O)NC3(CCN(C(C)C)CC3)N4)cc2)on1] | 4-(1'-isopropyl-4-oxo-3,4-dihydrospiro[benzo[e][1,3]oxazine-2,4'-piperidin]-6-yl)-N-((3-methylisoxazol-5-yl)methyl)benzamide |
| 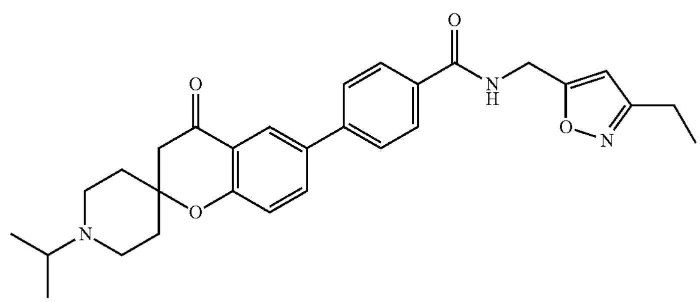 [SMILES: CCc1cc(CNC(=O)c2ccc(-c3ccc4c(c3)C(=O)CC3(CCN(C(C)C)CC3)O4)cc2)on1] | N-((3-ethylisoxazol-5-yl)methyl)-4-(1'-isopropyl-4-oxospiro[chroman-2,4'-piperidin]-6-yl)benzamide |
| 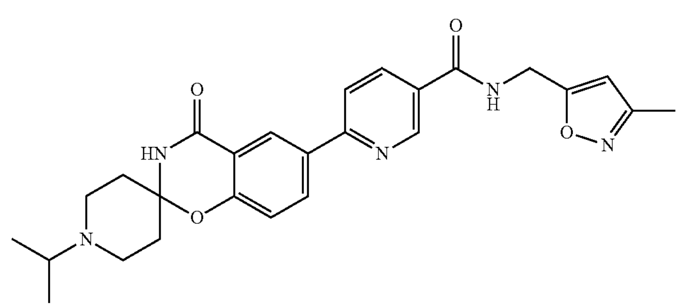 [SMILES: Cc1cc(CNC(=O)c2ccc(-c3ccc4c(c3)C(=O)NC3(CCN(C(C)C)CC3)O4)nc2)on1] | 6-(1'-isopropyl-4-oxo-3,4-dihydrospiro[benzo[e][1,3]oxazine-2,4'-piperidin]-6-yl)-N-((3-methylisoxazol-5-yl)methyl)nicotinamide |
| 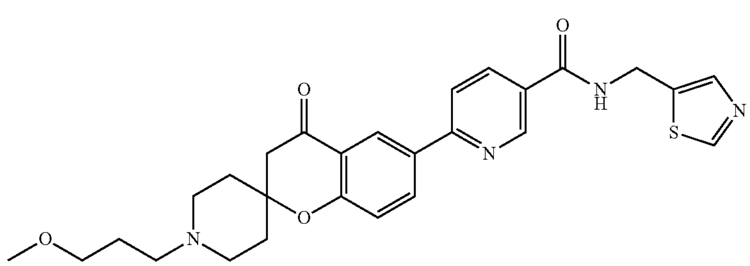 [SMILES: COCCCN1CCC2(CC1)CC(=O)c1cc(-c3ccc(C(=O)NCc4cncs4)cn3)ccc1O2] | 6-(1'-(3-methoxypropyl)-4-oxospiro[chroman-2,4'-piperidin]-6-yl)-N-(thiazol-5-ylmethyl)nicotinamide |

TABLE 1-continued

Additional Compounds of Formula (I)

| Structure | Compound Name |
| --- | --- |
| 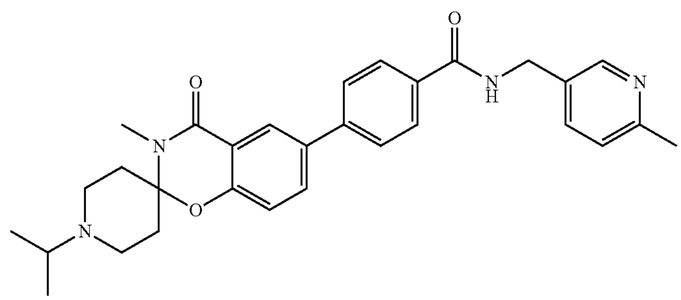 [SMILES: Cc1ccc(CNC(=O)c2ccc(-c3ccc4c(c3)C(=O)N(C)C3(CCN(C(C)C)CC3)O4)cc2)cn1] | 4-(1'-isopropyl-3-methyl-4-oxo-3,4-dihydrospiro[benzo[e][1,3]oxazine-2,4'-piperidin]-6-yl)-N-((6-methylpyridin-3-yl)methyl)benzamide |
| 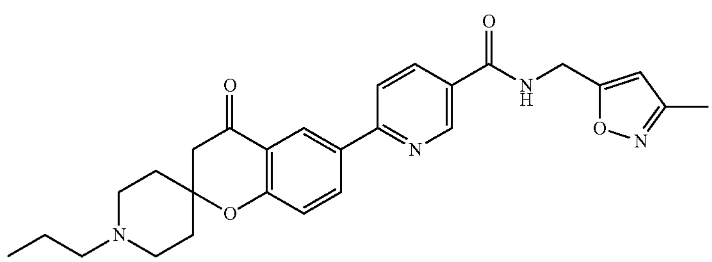 [SMILES: CCCN1CCC2(CC1)CC(=O)c1cc(-c3ccc(C(=O)NCc4cc(C)no4)cn3)ccc1O2] | N-((3-methylisoxazol-5-yl)methyl)-6-(4-oxo-1'-propylspiro[chroman-2,4'-piperidin]-6-yl)nicotinamide |
| 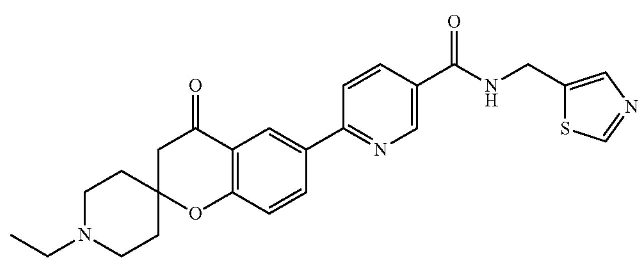 [SMILES: CCN1CCC2(CC1)CC(=O)c1cc(-c3ccc(C(=O)NCc4cncs4)cn3)ccc1O2] | 6-(1'-ethyl-4-oxospiro[chroman-2,4'-piperidin]-6-yl)-N-(thiazol-5-ylmethyl)nicotinamide |
| 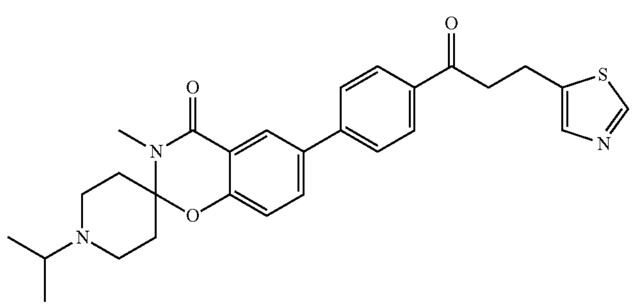 [SMILES: CC(C)N1CCC2(CC1)Oc1ccc(-c3ccc(C(=O)CCc4cncs4)cc3)cc1C(=O)N2C] | 1'-isopropyl-3-methyl-6-(4-(3-(thiazol-5-yl)propanoyl)phenyl)spiro[benzo[e][1,3]oxazine-2,4'-piperidin]-4(3H)-one |
| 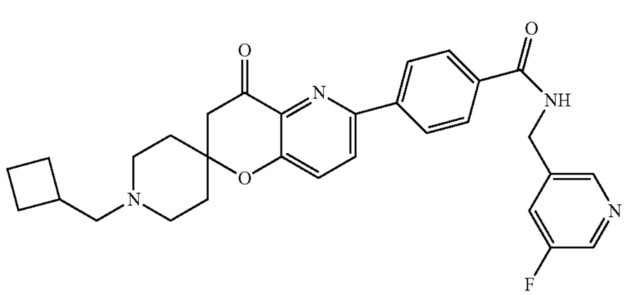 [SMILES: O=C(NCc1cncc(F)c1)c1ccc(-c2ccc3c(n2)C(=O)CC2(CCN(CC4CCC4)CC2)O3)cc1] | 4-(1-(cyclobutylmethyl)-4'-oxo-3',4'-dihydrospiro[piperidine-4,2'-pyrano[3,2-b]pyridin]-6'-yl)-N-((5-fluoropyridin-3-yl)methyl)benzamide |

TABLE 1-continued

Additional Compounds of Formula (I)

| Structure | Compound Name |
|---|---|
| 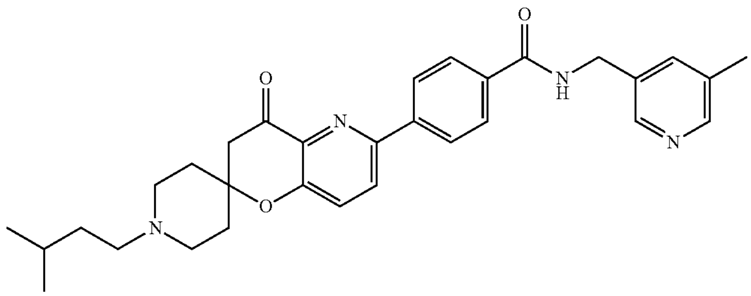 [SMILES: Cc1cncc(CNC(=O)c2ccc(-c3ccc4c(n3)C(=O)CC3(CCN(CCC(C)C)CC3)O4)cc2)c1] | N-((5-fluoropyridin-3-yl)methyl)-4-(1-isopentyl-4'-oxo-3',4'-dihydrospiro[piperidine-4,2'-pyrano[3,2-b]pyridin]-6'-yl)benzamide |
| | N-((5-fluoropyridin-3-yl)methyl)-6-(1'-(4-methoxybutyl)-4-oxospiro[chroman-2,4'-Fpiperidin]-6-yl)nicotinamide |
| 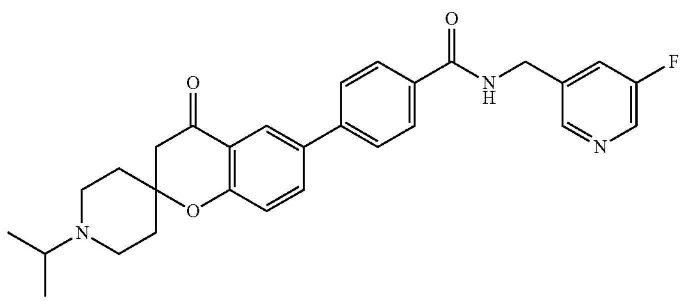 [SMILES: CC(C)N1CCC2(CC1)CC(=O)c1cc(-c3ccc(C(=O)NCc4cncc(F)c4)cc3)ccc1O2] | N-((5-fluoropyridin-3-yl)methyl)-4-(1'-isopropyl-4-oxospiro[chroman-2,4'-piperidin]-6-yl)benzamide |

Example 2: In Vitro Experiments

Example 2-1: Inhibition of NAMPT Enzymatic Activity

Recombinant NAMPT enzyme (MBL) was briefly preincubated in the absence or presence of inhibitor followed by addition of nicotinamide. Enzymatic reaction was allowed to proceed for 6 hours at 37° C. Reaction was terminated and NMN reaction product detected using the method as described in: Zhang R Y, Qin Y, Lv X Q, Wang P, Xu T Y, Zhang L, Miao C Y., Anal. Biochem. 2011 May 1; 412(1):18-25.

The 50% inhibitory concentration ($IC_{50}$) is the concentration at which 50% of the maximal activity was inhibited.

The results from this assay for representative compounds are presented in Table 2 below.

Example 2-2: Anti-Proliferative Activity on B Cells

Fresh primary human B cells obtained from Analytical Biological Services (Wilmington, Del.) were diluted to $1 \times 10^{\wedge}6$ cells per ml in AIM-V medium (Invitrogen), and stimulated with anti-IgM (10 ug/ml) (KPL) in the absence or presence of inhibitor for 72 hours at 37° C./5% $CO_2$ prior to viability determination using CellTiterGlo (Promega) per manufacturer's instruction.

The 50% inhibitory concentration ($IC_{50}$) is the concentration at which 50% of the maximal activity was inhibited.

The results from this assay for representative compounds are presented in Table 2 below.

Example 2-3: Anti-Proliferative Activity on T Cells

Fresh primary human T cells obtained from Analytical Biological Services (Wilmington, Del.) were diluted to $1 \times 10^{\wedge}6$ cells per ml in AIM-V medium (Invitrogen), and stimulated with CD3/CD28 beads (Invitrogen) in the absence or presence of inhibitor for 72 hours at 37° C./5% $CO_2$ prior to viability determination using CellTiterGlo (Promega) per manufacturer's instruction.

The 50% inhibitory concentration ($IC_{50}$) is the concentration at which 50% of the maximal activity was inhibited.

The results from this assay for representative compounds are presented in Table 2 below.

TABLE 2

NAMPT, B Cell and T Cell IC$_{50}$ for Selected Compounds

| Compound Name | NAMPT IC$_{50}$ (μM) | B CELL IC$_{50}$ (μM) | T CELL IC$_{50}$ (μM) |
|---|---|---|---|
| 1'-isopropyl-3-methyl-6-(4-(3-(thiazol-5-yl)propanoyl)phenyl)spiro[benzo[e][1,3]oxazine-2,4'-piperidin]-4(3H)-one | 0.1661 | 0.0408 | 3.1938 |
| 4-(1'-isopropyl-4-oxospiro[chroman-2,4'-piperidin]-6-yl)-N-((3-methylisoxazol-5-yl)methyl)benzamide | 0.0009 | 0.0227 | 4.3750 |
| N-((5-fluoropyridin-3-yl)methyl)-4-(1'-isopropyl-4-oxospiro[chroman-2,4'-piperidin]-6-yl)benzamide | 0.0055 | 0.0079 | 3.2994 |
| 6-(1'-isopropyl-4-oxospiro[chroman-2,4'-piperidin]-6-yl)-N-((1-methyl-1H-pyrazol-4-yl)methyl)nicotinamide | 0.0140 | 0.0598 | 5.5853 |
| 6-(4-oxo-1'-propylspiro[chroman-2,4'-piperidin]-6-yl)-N-(thiazol-5-ylmethyl)nicotinamide | 0.0667 | 0.0152 | 1.0775 |
| (1'-butyl-4-oxospiro[chroman-2,4'-piperidin]-6-yl)-N-(thiazol-5-ylmethyl)nicotinamide | 0.0299 | 0.0248 | 1.8800 |
| 3-fluoro-4-(1'-isopropyl-4-oxospiro[chroman-2,4'-piperidin]-6-yl)-N-((6-methylpyridin-3-yl)methyl)benzamide | 0.0020 | 0.0539 | 8.5138 |
| N-((3-methylisoxazol-5-yl)methyl)-4-(4-oxo-1'-propylspiro[chroman-2,4'-piperidin]-6-yl)benzamide | 0.0020 | 0.0129 | 0.6769 |
| N-((5-fluoropyridin-3-yl)methyl)-4-(4-oxo-1'-propylspiro[chroman-2,4'-piperidin]-6-yl)benzamide | 0.0030 | 0.0074 | 1.9653 |
| 4-(1'-isopropyl-4-oxospiro[chroman-2,4'-piperidin]-6-yl)-N-((5-methylisoxazol-3-yl)methyl)benzamide | 0.0010 | 0.0113 | 3.2428 |
| N-((3-methylisoxazol-5-yl)methyl)-6-(1'-propylspiro[chromene-2,4'-piperidin]-6-yl)nicotinamide | 0.0010 | 0.0044 | 0.3417 |
| 6-(1'-(3-methoxypropyl)spiro[chromene-2,4'-piperidin]-6-yl)-N-(thiazol-5-ylmethyl)nicotinamide | 0.0564 | 0.0455 | 5.7920 |
| N-((3-methylisoxazol-5-yl)methyl)-6-(1'-((3-methyloxetan-3-yl)methyl)-4-oxospiro[chroman-2,4'-piperidin]-6-yl)nicotinamide | 0.0030 | 0.0313 | 11.6673 |
| N-((3-methylisoxazol-5-yl)methyl)-6-(1'-((3-methyloxetan-3-yl)methyl)-4-oxospiro[chroman-2,4'-piperidin]-6-yl)nicotinamide | 0.0014 | 0.0118 | 5.3998 |
| N-((2-fluoropyridin-3-yl)methyl)-4-(1'-isopropyl-4-oxospiro[chroman-2,4'-piperidin]-6-yl)benzamide | 0.0010 | 0.0099 | 5.7883 |
| N-butoxy-6-(1'-isopropyl-4-oxospiro[chroman-2,4'-piperidin]-6-yl)nicotinamide | 0.0014 | 0.0450 | 7.3731 |
| N-((5-fluoropyridin-3-yl)methyl)-6-(1'-(4-methoxybutyl)-4-oxospiro[chroman-2,4'-piperidin]-6-yl)nicotinamide | 0.0042 | 0.0109 | 5.4532 |
| 4-(1'-isopropyl-4-oxo-3,4-dihydrospiro[benzo[e][1,3]oxazine-2,4'-piperidin]-6-yl)-N-((3-methylisoxazol-5-yl)methyl)benzamide | 0.0040 | 0.0334 | 5.6776 |
| 4-(1-(cyclobutylmethyl)-4'-oxo-3',4'-dihydrospiro[piperidine-4,2'-pyrano[3,2-b]pyridin]-6'-yl)-N-((5-fluoropyridin-3-yl)methyl)benzamide | 0.0664 | 0.0830 | 3.9880 |
| N-((3-ethylisoxazol-5-yl)methyl)-4-(1'-isopropyl-4-oxospiro[chroman-2,4'-piperidin]-6-yl)benzamide | 0.0010 | 0.0213 | 1.7222 |
| N-((5-fluoropyridin-3-yl)methyl)-4-(1-isopentyl-4'-oxo-3',4'-dihydrospiro[piperidine-4,2'-pyrano[3,2-b]pyridin]-6'-yl)benzamide | 0.1274 | 0.1068 | 9.6657 |
| N-((5-fluoropyridin-3-yl)methyl)-4-(1'-isopropyl-3-methyl-4-oxo-3,4-dihydrospiro[benzo[e][1,3]oxazine-2,4'-piperidin]-6-yl)benzamide | 0.0035 | 0.0060 | 0.9997 |
| 6-(1'-isopropyl-4-oxo-3,4-dihydrospiro[benzo[e][1,3]oxazine-2,4'-piperidin]-6-yl)-N-((3-methylisoxazol-5-yl)methyl)nicotinamide | 0.0030 | 0.0292 | 14.6143 |

TABLE 2-continued

NAMPT, B Cell and T Cell IC$_{50}$ for Selected Compounds

| Compound Name | NAMPT IC$_{50}$ (μM) | B CELL IC$_{50}$ (μM) | T CELL IC$_{50}$ (μM) |
|---|---|---|---|
| 6-(1'-(3-methoxypropyl)-4-oxospiro[chroman-2,4'-piperidin]-6-yl)-N-(thiazol-5-ylmethyl)nicotinamide | 0.1409 | 0.0438 | 3.2900 |
| 6-(1'-isopropyl-3-methyl-4-oxo-3,4 dihydrospiro[benzo[e][1,3]oxazine-2,4'-piperidin]-6-yl)-N-(thiazol-5-ylmethyl)nicotinamide | 0.1071 | 0.0254 | 1.5503 |
| 4-(1'-isopropyl-3-methyl-4-oxo-3,4-dihydrospiro[benzo[e][1,3]oxazine-2,4'-piperidin]-6-yl)-N-((6-methylpyridin-3-yl)methyl)benzamide | 0.0020 | 0.0153 | 4.6159 |
| N-((3-methylisoxazol-5-yl)methyl)-6-(4-oxo-1'-propylspiro[chroman-2,4'-piperidin]-6-yl)nicotinamide | 0.0010 | 0.0059 | 0.7308 |
| 6-(1'-isopropyl-3-methyl-4-oxo-3,4-dihydrospiro[benzo[e][1,3]oxazine-2,4'-piperidin]-6-yl)-N-((1-methyl-1H-pyrazol-4-yl)methyl)nicotinamide | 0.0150 | 0.0977 | 6.1082 |
| 6-(1'-ethyl-4-oxospiro[chroman-2,4'-piperidin]-6-yl)-N-(thiazol-5-ylmethyl)nicotinamide | 0.2708 | 0.0509 | 3.3550 |
| 6-(1'-isopropyl-3-methyl-4-oxo-3,4-dihydrospiro[benzo[e][1,3]oxazine-2,4'-piperidin]-6-yl)-N-((3-methylisoxazol-5-yl)methyl)nicotinamide | 0.0020 | 0.0095 | 1.1806 |

Example 2-4: Activity on Various Cell Lines

Leukemia/Lymphoma cell lines (ATCC) were diluted in vendor-recommended media and incubated in the absence or presence of inhibitor for 72 hours at 37° C./5% $CO_2$ prior to viability determination using CellTiterGlo (Promega) per manufacturer's instruction. The human cell lines studied include acute T-cell leukemia (JURKAT), chronic myelogenous leukemia (K562), and B-cell acute lymphocytic leukemia (NALM6 and SUP-B15).

The anti-proliferative activity on these cell lines for selected compounds is presented in Table 3 below.

TABLE 3

Anti-Proliferative Activity on Various Cell Line Activity for Selected Compounds

| Compound Name | JURKAT | K562 | NALM6 | SUP-B15 |
|---|---|---|---|---|
| 1'-isopropyl-3-methyl-6-(4-(3-(thiazol-5-yl)propanoyl)phenyl)spiro[benzo[e][1,3]oxazine-2,4'-piperidin]-4(3H)-one | 0.034727 | 0.111998 | 0.018604 | 0.002847 |
| 4-(1'-isopropyl-4-oxospiro[chroman-2,4'-piperidin]-6-yl)-N-((3-methylisoxazol-5-yl)methyl)benzamide | 0.017937 | 0.068117 | 0.015026 | 0.002439 |
| N-((5-fluoropyridin-3-yl)methyl)-4-(1'-isopropyl-4-oxospiro[chroman-2,4'-piperidin]-6-yl)benzamide | 0.020351 | 0.078792 | 0.008799 | 0.001097 |
| 6-(1'-isopropyl-4-oxospiro[chroman-2,4'-piperidin]-6-yl)-N-((1-methyl-1H-pyrazol-4-yl)methyl)nicotinamide | 0.209499 | 0.3045 | 0.102349 | 0.014141 |
| 6-(4-oxo-1'-propylspiro[chroman-2,4'-piperidin]-6-yl)-N-(thiazol-5-ylmethyl)nicotinamide | 0.016292 | 0.0357 | 0.01188 | 0.001894 |
| (1'-butyl-4-oxospiro[chroman-2,4'-piperidin]-6-yl)-N-(thiazol-5-ylmethyl)nicotinamide | 0.008845 | 0.01977 | 0.005734 | 0.00103 |
| 3-fluoro-4-(1'-isopropyl-4-oxospiro[chroman-2,4'-piperidin]-6-yl)-N-((6-methylpyridin-3-yl)methyl)benzamide | 0.021286 | 1.734128 | 0.010666 | 0.002218 |
| N-((3-methylisoxazol-5-yl)methyl)-4-(4-oxo-1'-propylspiro[chroman-2,4'-piperidin]-6-yl)benzamide | 0.007779 | 0.024999 | 0.006739 | 0.002069 |
| N-((5-fluoropyridin-3-yl)methyl)-4-(4-oxo-1'-propylspiro[chroman-2,4'-piperidin]-6-yl)benzamide | 0.007074 | 0.018673 | 0.003155 | 0.000556 |
| 4-(1'-isopropyl-4-oxospiro[chroman-2,4'-piperidin]-6-yl)-N-((5-methylisoxazol-3-yl)methyl)benzamide | 0.010663 | 0.063619 | 0.002695 | 0.001172 |
| N-((3-methylisoxazol-5-yl)methyl)-6-(1'-propylspiro[chromene-2,4'-piperidin]-6-yl)nicotinamide | 0.00638 | 0.0258 | 0.00363 | 0.001036 |

TABLE 3-continued

Anti-Proliferative Activity on Various Cell Line Activity for Selected Compounds

| Compound Name | JURKAT | K562 | NALM6 | SUP-B15 |
| --- | --- | --- | --- | --- |
| 6-(1'-(3-methoxypropyl)spiro[chromene-2,4'-piperidin]-6-yl)-N-(thiazol-5-ylmethyl)nicotinamide | | 0.0858 | 0.013857 | 0.001697 |
| N-((3-methylisoxazol-5-yl)methyl)-6-(1'-((3-methyloxetan-3-yl)methyl)-4-oxospiro[chroman-2,4'-piperidin]-6-yl)nicotinamide | 0.0393 | 0.829 | 0.024854 | 0.003771 |
| N-((3-methylisoxazol-5-yl)methyl)-6-(1'-((3-methyloxetan-3-yl)methyl)-4-oxospiro[chroman-2,4'-piperidin]-6-yl)nicotinamide | 0.013556 | 0.077811 | 0.008449 | 0.001764 |
| N-((2-fluoropyridin-3-yl)methyl)-4-(1'-isopropyl-4-oxospiro[chroman-2,4'-piperidin]-6-yl)benzamide | 0.003659 | 0.00294 | 0.003481 | 0.00147 |
| N-butoxy-6-(1'-isopropyl-4-oxospiro[chroman-2,4'-piperidin]-6-yl)nicotinamide | 0.0233 | 0.281968 | 0.0156 | 0.003019 |
| N-((5-fluoropyridin-3-yl)methyl)-6-(1'-(4-methoxybutyl)-4-oxospiro[chroman-2,4'-piperidin]-6-yl)nicotinamide | 0.012051 | 0.029438 | 0.00483 | 0.000847 |
| 4-(1'-isopropyl-4-oxo-3,4-dihydrospiro[benzo[e][1,3]oxazine-2,4'-piperidin]-6-yl)-N-((3-methylisoxazol-5-yl)methyl)benzamide | 0.042114 | 0.350422 | 0.023575 | 0.004112 |
| 4-(1-(cyclobutylmethyl)-4'-oxo-3',4'-dihydrospiro[piperidine-4,2'-pyrano[3,2-b]pyridin]-6'-yl)-N-((5-fluoropyridin-3-yl)methyl)benzamide | 0.154 | 0.332 | 0.0489 | 0.00729 |
| N-((3-ethylisoxazol-5-yl)methyl)-4-(1'-isopropyl-4-oxospiro[chroman-2,4'-piperidin]-6-yl)benzamide | 0.012171 | 0.044702 | 0.00742 | 0.002295 |
| N-((5-fluoropyridin-3-yl)methyl)-4-(1-isopentyl-4'-oxo-3',4'-dihydrospiro[piperidine-4,2'-pyrano[3,2-b]pyridin]-6'-yl)benzamide | 0.203 | 0.822 | 0.174 | 0.0129 |
| N-((5-fluoropyridin-3-yl)methyl)-4-(1'-isopropyl-3-methyl-4-oxo-3,4-dihydrospiro[benzo[e][1,3]oxazine-2,4'-piperidin]-6-yl)benzamide | 0.007037 | 0.028286 | 0.003564 | 0.000606 |
| 6-(1'-isopropyl-4-oxo-3,4-dihydrospiro[benzo[e][1,3]oxazine-2,4'-piperidin]-6-yl)-N-((3-methylisoxazol-5-yl)methyl)nicotinamide | 0.024793 | 0.875806 | 0.0171 | 0.003192 |
| 6-(1'-(3-methoxypropyl)-4-oxospiro[chroman-2,4'-piperidin]-6-yl)-N-(thiazol-5-ylmethyl)nicotinamide | 0.019627 | 0.054381 | 0.009382 | 0.001833 |
| 6-(1'-isopropyl-3-methyl-4-oxo-3,4-dihydrospiro[benzo[e][1,3]oxazine-2,4'-piperidin]-6-yl)-N-(thiazol-5-ylmethyl)nicotinamide | 0.032986 | 0.075684 | 0.01763 | 0.002135 |
| 4-(1'-isopropyl-3-methyl-4-oxo-3,4-dihydrospiro[benzo[e][1,3]oxazine-2,4'-piperidin]-6-yl)-N-((6-methylpyridin-3-yl)methyl)benzamide | 0.00767 | 0.028299 | 0.005259 | 0.000663 |
| N-((3-methylisoxazol-5-yl)methyl)-6-(4-oxo-1'-propylspiro[chroman-2,4'-piperidin]-6-yl)nicotinamide | 0.003542 | 0.019439 | 0.002255 | 0.000706 |
| 6-(1'-isopropyl-3-methyl-4-oxo-3,4-dihydrospiro[benzo[e][1,3]oxazine-2,4'-piperidin]-6-yl)-N-((1-methyl-1H-pyrazol-4-yl)methyl)nicotinamide | 0.18092 | 0.628968 | 0.121959 | 0.020856 |
| 6-(1'-ethyl-4-oxospiro[chroman-2,4'-piperidin]-6-yl)-N-(thiazol-5-ylmethyl)nicotinamide | 0.043571 | 0.180278 | 0.021589 | 0.00515 |
| 6-(1'-isopropyl-3-methyl-4-oxo-3,4-dihydrospiro[benzo[e][1,3]oxazine-2,4'-piperidin]-6-yl)-N-((3-methylisoxazol-5-yl)methy)nicotinamide | 0.016592 | 0.04761 | 0.006144 | 0.001508 |

Example 2-5: Mechanism of Action

Sup-B15 cells (ATCC) were incubated in media lacking or containing 200 μM nicotinamide mononucleotide (NMN) (Sigma) in the absence or presence of inhibitor for 72 hours at 37° C./5% $CO_2$ prior to viability determination using CellTiterGlo (Promega) per manufacturer's instruction.

Chemical proteomics. Sup-B15 cell extract was incubated with a biotinylated derivative of 4-(1'-isopropyl-4-oxospiro[chroman-2,4'-piperidin]-6-yl)-N-((3-methylisoxazol-5-yl)methyl)benzamide, followed by collection of compound/ protein complexes with streptavidin beads (Invitrogen). Following extensive washing, bound proteins were eluted using free (non-biotinylated) 4-(1'-isopropyl-4-oxospiro [chroman-2,4'-piperidin]-6-yl)-N-((3-methylisoxazol-5-yl) methyl)benzamide or an inactive analog. Following SDS-PAGE, one prominent band was excised and identified by LC/MS as NAMPT.

The molecular target of 4-(1'-isopropyl-4-oxospiro[chroman-2,4'-piperidin]-6-yl)-N-((3-methylisoxazol-5-yl) methyl)benzamide is nicotinamide phosphoribosyl transferase (NAMPT), the product of which is nicotinamide mononucleotide (NMN). The anti-proliferative activity of 4-(1'-isopropyl-4-oxospiro[chroman-2,4'-piperidin]-6-yl)-N-((3-methylisoxazol-5-yl)methyl)benzamide is counteracted by NMN, and 4-(1'-isopropyl-4-oxospiro[chroman-2,4'-piperidin]-6-yl)-N-((3-methylisoxazol-5-yl)methyl) benzamide potently inhibits NAMPT enzyme activity. On-target, selective anti-proliferative activity was maintained throughout the medicinal chemistry campaign, as all members of Formula (I) 45 series are rescuable with NMN (FIG. 1).

Example 2-6: Activity on Influenza and RSV Infected Cells

To determine respiratory syncytial virus (RSV) inhibition, Vero cells are plated in 96 well plates to a confluency of 80%. Compounds are added at half log dilutions starting at 10 uM down to 3 nM in triplicate and allowed to incubate with cells for one hour. Virus is added to the wells at an MOI of 10 and allowed to replicate for 72 hours. Viable cells protected from virus induced cytopathic effect (CPE) are detected using a fluorescent vital dye. The ECso of the inhibition of CPE is determined using a robust fit methodology.

To determine influenza virus inhibition, MDCK cells are plated in 96 well plates to a confluency of 80%. Compounds are added at half log dilutions starting at 10 μM down to 3 nM in triplicate and allowed to incubate with cells for one hour. Virus is added to the wells at an MOI of 10 and allowed to replicate for 72 hours. Viable cells protected from virus induced cytopathic effect (CPE) are detected using a fluorescent vital dye. The ECso of the inhibition of CPE is determined using a robust fit methodology.

Example 3: In Vivo Experiments

Example 3-1: Pharmacokinetic Studies

Example 3-1-a: Oral and Intravenous Pharmacokinetics in Sprague-Dawley Rats

The oral (PO) and intravenous (IV) pharmacokinetics of test compounds, 1'-isopropyl-3-methyl-6-(4-(3-(thiazol-5-yl)propanoyl)phenyl)spiro[benzo[e][1,3]oxazine-2,4'-piperidin]-4(3H)-one and 4-(1'-isopropyl-4-oxospiro[chroman-2,4'-piperidin]-6-yl)-N-((3-methylisoxazol-5-yl)methyl) benzamide, was evaluated in male Sprague-Dawley Rats. An overview of the study design is presented in Table 4 below. Blood samples were collected prior to test compound dosing. Animals were dosed at $T_0$; subsequent blood samples were collected 2, 5, 15, and 30 minutes and 1, 2, 4, 6, 8, and 24 hours post-dosing. The blood samples were collected via jugular vein cannula. The samples were centrifuged at 13,000 rpm at 4° C. for 5 minutes. Plasma samples were collected into a 96-well plate after centrifugation of the blood samples. The plasma concentrations of test compounds were analyzed by LC-MS/MS.

TABLE 4

Rat Pharmacokinetics Study Design

| Test Compound | Cohort | Route of Administration | Number of Animals | Dose (mg/kg) |
|---|---|---|---|---|
| 4-(1'-isopropyl-4-oxospiro[chroman-2,4'-piperidin]-6-yl)-N-((3-methylisoxazol-5-yl)methyl)benzamide | 1<br>2 | IV<br>Oral | 2<br>3 | 1<br>3 |
| 1'-isopropyl-3-methyl-6-(4-(3-(thiazol-5-yl)propanoyl)phenyl)spiro[benzo[e][1,3]oxazine-2,4'-piperidin]-4(3H)-one | 3<br>4 | IV<br>Oral | 2<br>3 | 1<br>3 |

Figure 2:
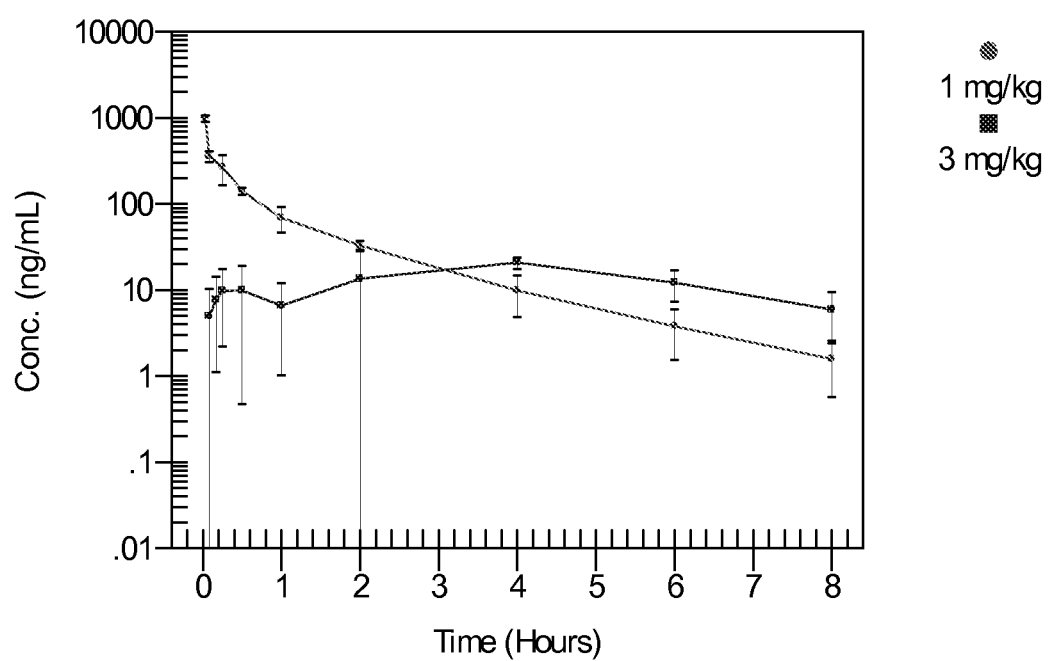
FIG. 2 is a graph showing the mean plasma concentration vs. time for 1'-isopropyl-3-methyl-6-(4-(3-(thiazol-5-yl)propanoyl)phenyl)spiro-[benzo[e][1,3]oxazine-2,4'-piperidin]-4(3H)-one following intravenous or oral administration to rat.
Figure 3:
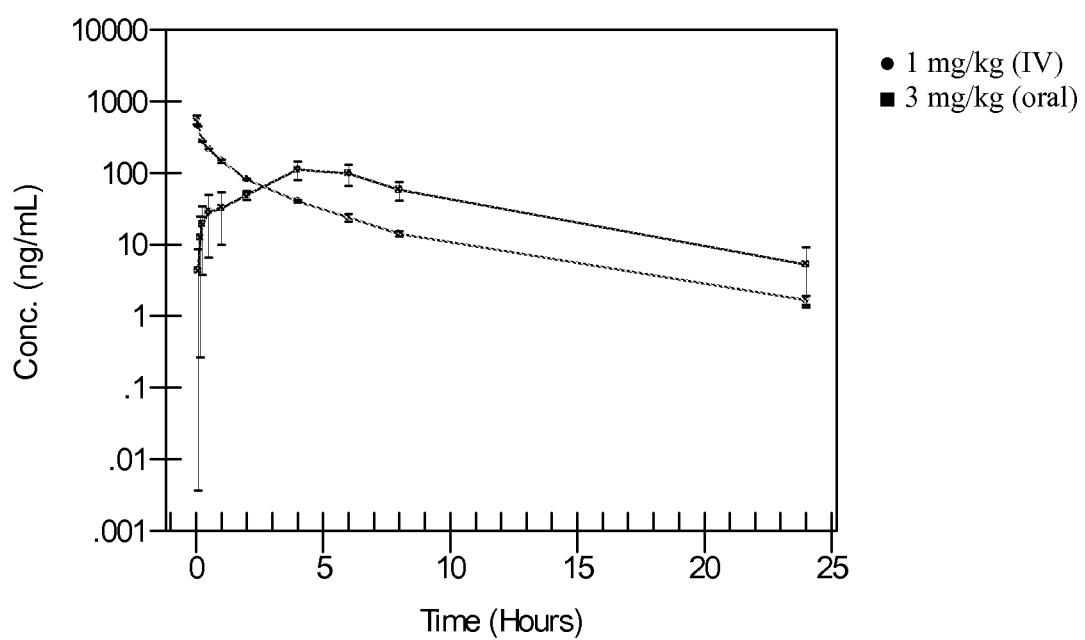
FIG. 3 is a graph showing the mean plasma concentration vs. time for 4-(1'-isopropyl-4-oxospiro[chroman-2,4'-piperidin]-6-yl)-N-((3-methylisoxazol-5-yl)methyl)benzamide following intravenous or oral administration to rat.

The test compounds, both intravenously and orally administered, were well-tolerated. No adverse physical abnormalities were observed. A graphical comparison of the oral plasma concentrations compared to intravenous plasma concentrations, as measured over time, for the test compounds are presented in FIG. 2 and FIG. 3.

Example 3-1-b: Oral and Intravenous Pharmacokinetics in Mice

The oral and intravenous pharmacokinetics of test compound 4-(1'-isopropyl-4-oxospiro[chroman-2,4'-piperidin]-6-yl)-N-((3-methylisoxazol-5-yl)methyl)benzamide was evaluated in female NOD.Cg-Prkdc$^{scid}$Il2r$^{gtm1WJl}$/SzJ mice. An overview of the study design is presented in Table 5 below. Blood samples were collected prior to test compound dosing, at specified time points after dosing, and after animal sacrifice. The in life blood samples were collected by tail snip or facial vein; terminal blood samples were collected via cardiac puncture following inhalation anesthesia. The samples were collected into K2EDTA tubes and stored on wet ice until proceeding to plasma by centrifugation at 3000 g at 5° C. within 1 hour of collection. Plasma samples were collected into 96-well plates after centrifugation and stored at −80° C. The plasma concentrations of test compounds were analyzed by LC-MS/MS.

TABLE 5

| | | | | | Terminal |
| | | Number | | | Sample |
| | Route of | of | Dose | In Life Sample | Collection |
| Cohort | Administration | Animals | (mg/kg) | Collection Time Points | Time Point |
| --- | --- | --- | --- | --- | --- |
| 1(a) | IV | 3 | 1 | 5 min, 30 min, 2 hours | 8 hours |
| 1(b) | IV | 3 | 1 | 10 min, 1 hour, 4 hours | 24 hours |
| 2(a) | Oral | 3 | 5 | 5 min, 30 min, 2 hours | 8 hours |
| 2(b) | Oral | 3 | 5 | 10 min, 1 hour, 4 hours | 24 hours |
| 3(a) | Oral | 3 | 10 | 5 min, 30 min, 2 hours | 8 hours |
| 3(b) | Oral | 3 | 10 | 10 min, 1 hour, 4 hours | 24 hours |
| 4(a) | Oral | 3 | 20 | 5 min, 30 min, 2 hours | 8 hours |
| 4(b) | Oral | 3 | 20 | 10 min, 1 hour, 4 hours | 24 hours |

Mouse Pharmacokinetics Study Design

Figure 4:
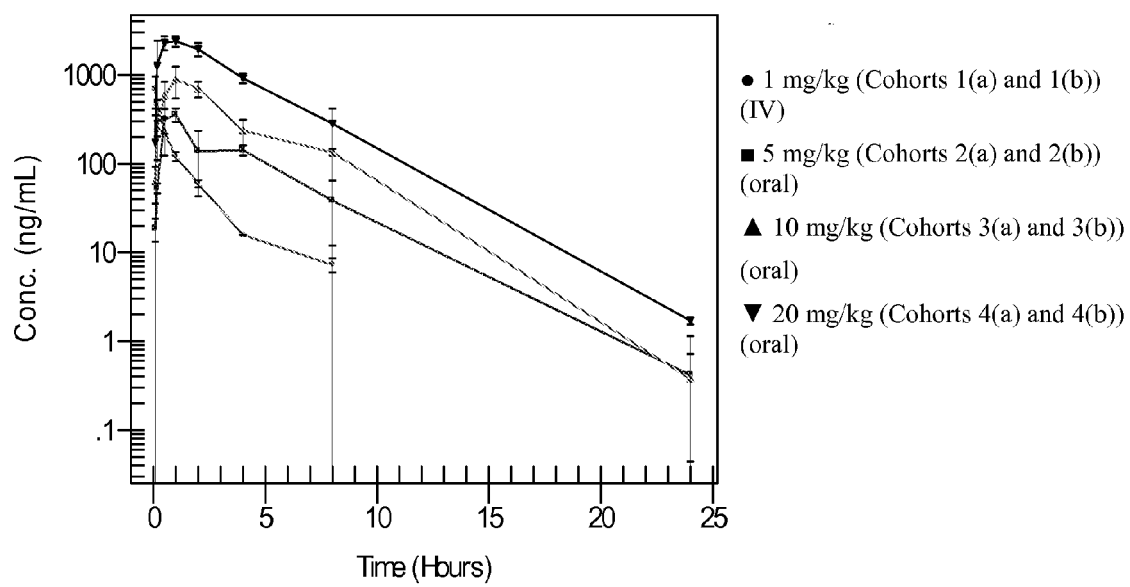
FIG. 4 is a graph showing the mean plasma concentration vs. time for 4-(1'-isopropyl-4-oxospiro[chroman-2,4'-piperidin]-6-yl)-N-((3-methylisoxazol-5-yl)methyl)benzamide following intravenous or oral administration to mouse.

No significant clinical signs were observed during the course of the study. A graphical comparison of the oral plasma concentrations compared to intravenous plasma concentrations, as measured over time, for the test compound is presented in FIG. 4.

Example 3-2: Efficacy Studies

Figure 5:
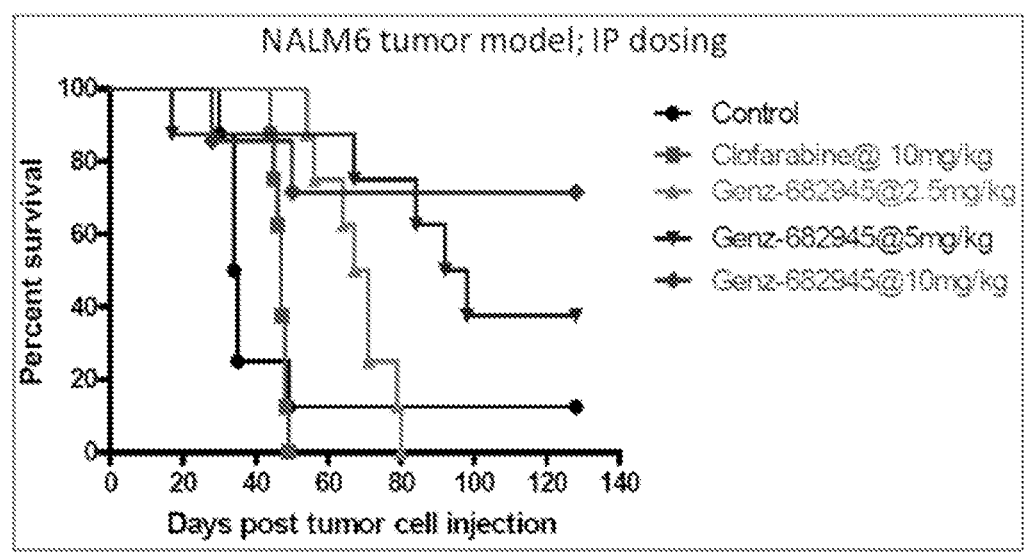
FIG. 5 is a graph showing in vivo assay results of 4-(1'-isopropyl-4-oxospiro[chroman-2,4'-piperidin]-6-yl)-N-((3-methylisoxazol-5-yl)methyl)benzamide in NALM6 leukemia model.
Figure 6:
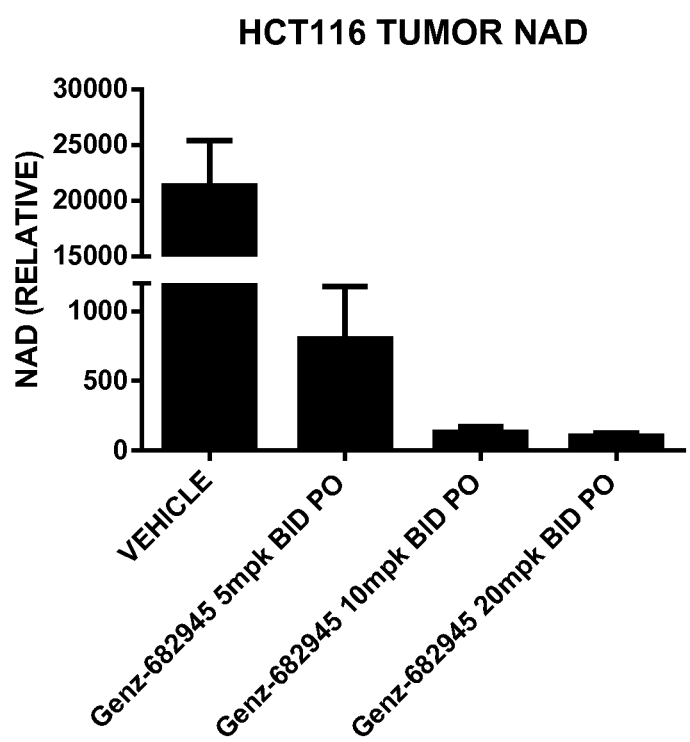
FIG. 6 is a graph showing in vivo assay results of 4-(1'-isopropyl-4-oxospiro[chroman-2,4'-piperidin]-6-yl)-N-((3-methylisoxazol-5-yl)methyl)benzamide in a HCT116 tumor model.

Example 3-2-a: NALM6 Leukemia Study 4-(1'-isopropyl-4-oxospiro[chroman-2,4'-piperidin]-6-yl)-N-((3-methylisoxazol-5-yl)methyl)benzamide was tested in the NALM6 leukemia model. As shown in FIG. 6, IP dosing of 4-(1'-isopropyl-4-oxospiro[chroman-2,4'-piperidin]-6-yl)-N-((3-methylisoxazol-5-yl)methyl)benzamide (also known as GENZ-682945) produced a significant survival benefit in this xenograft model, in excess of the standard of care (clofarabine). $5 \times 10^{\wedge}6$ NALM-6 cells were injected via tail vein into female CB17SCID/Crl mice (Charles River). One week later, 4-(1'-isopropyl-4-oxospiro[chroman-2,4'-piperidin]-6-yl)-N-((3-methylisoxazol-5-yl)methyl)benzamide was administered by i.p. injection twice daily for 35 days. Clofarabine was administered once daily by i.p. injection once daily for 5 days for four weeks. Study endpoint was survival time, and mice were sacrificed upon appearance of systemic signs of severe disease such as paralysis or cachexia. The results are shown in FIG. 5.

Example 3-2-b: HCT116 Tumor Growth Study

Tumor Growth Study: Female athymic nude mice (Crl:NU(Ncr)-Foxn1nu, Charles River) (n=10/group) were injected with $5 \times 10^6$ HCT116 cells, and treatment was initiated at average tumor size of 100 mm$^3$. 4-(1'-isopropyl-4-oxospiro[chroman-2,4'-piperidin]-6-yl)-N-((3-methylisoxazol-5-yl)methyl)benzamide and vehicle control were administered orally twice daily for 8 days. Tumor size was measured twice weekly with calipers.

Tumor NAD measurement: Female athymic nude mice (Crl:NU(Ncr)-Foxn1nu, Charles River) (n=3/group) were injected with $5 \times 10^6$ HCT116 cells, and treatment was initiated at tumor size of 250-400 mm$^3$. 4-(1'-isopropyl-4-oxospiro[chroman-2,4'-piperidin]-6-yl)-N-((3-methylisoxazol-5-yl)methyl)benzamide and vehicle control were administered orally twice daily for 1.5 days (3 doses). Six hours post last dose, tumors were excised, washed, sectioned, weighted, and snap frozen. Tumor portions were extracted in ethanol/PBS (90:10) by three cycles of rapid freeze/thaw/sonication, prior to analysis for NAD content by LC/MS. The data are presented in FIG. 6.

Figure 7:
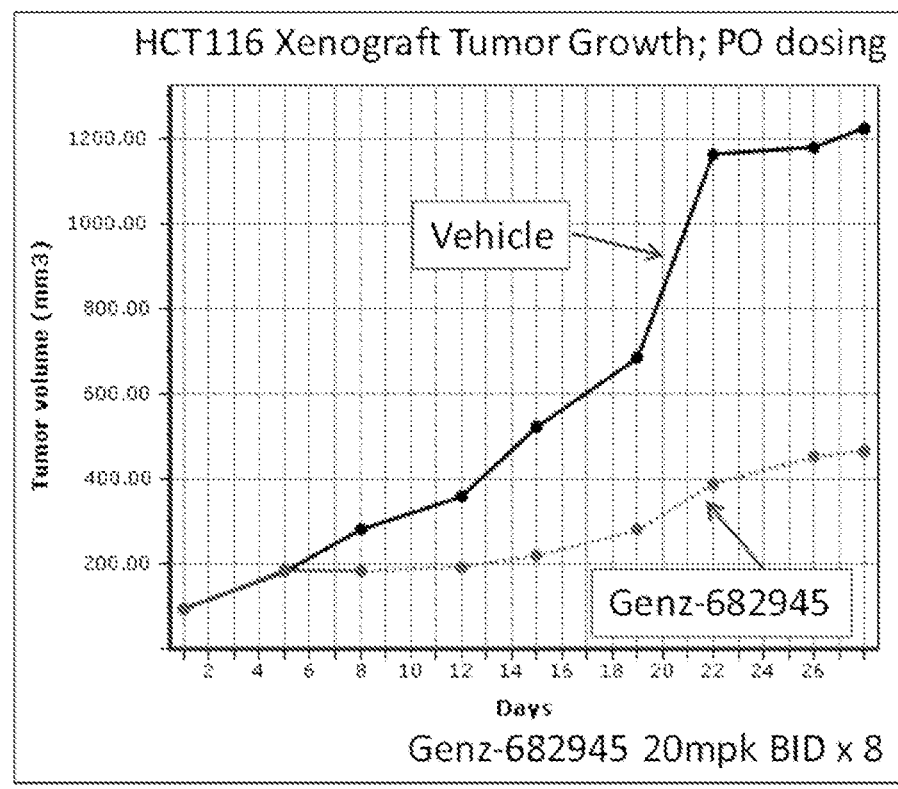
FIG. 7 is a graph showing in vivo assay results of 4-(1'-isopropyl-4-oxospiro[chroman-2,4'-piperidin]-6-yl)-N-((3-methylisoxazol-5-yl)methyl)benzamide in another HCT116 tumor model.

4-(1'-isopropyl-4-oxospiro[chroman-2,4'-piperidin]-6-yl)-N-((3-methylisoxazol-5-yl)methyl)benzamide was also tested in the HCT116 solid tumor model. Twice-daily oral dosing of 4-(1'-isopropyl-4-oxospiro[chroman-2,4'-piperidin]-6-yl)-N-((3-methylisoxazol-5-yl)methyl)benzamide produced a significant tumor growth delay (FIG. 7), which persisted for at least one week after dosing was stopped due to 10% mortality in the treated group.

IV. Formulation, Dosage Forms and Administration

When employed as pharmaceuticals, the compounds of the invention can be administered in the form of pharmaceutical compositions. Thus the present disclosure provides a composition comprising a compound of Formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinyl pyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; and sweetening agents and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition.

In some embodiments, a dry granulation process is used to produce the composition. The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient.

In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade).

Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose rang 5 e is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or sy 5 stemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner. Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline® (petroleum jelly) and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes as set forth in set forth in Example 2: In vitro Experiments and Example 3: In vivo Experiments. Thus, another aspect of the present invention relates to labeled compounds of the invention (radio-labeled, fluorescent-labeled, etc.) that would be useful not only in imaging techniques but also in assays, both in vitro and in vivo, for localizing and quantitating NAMPT in tissue samples, including human, and for identifying NAMPT ligands by inhibition binding of a labeled compound. Accordingly, the present invention includes NAMPT assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides (i.e., radioactive isotopes) that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro Pim kinase labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind NAMPT by monitoring its concentration variation when contacting with NAMPT, through tracking of the labeling. For example, a test compound (labeled) can be evaluated for its ability to reduce binding of another compound which is known to bind to NAMPT (i.e., standard compound). Accordingly, the ability of a test compound to compete with the standard compound for binding to NAMPT directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention NAMPT-associated diseases or disorders, such as cancer, which include one or more containers containing a pharmaceutical composition comprising a therapeutically effective amount of a compound of formula (I), or any of the embodiments thereof. Such kits can further include one or more of various conventional pharmaceutical kit components, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula (I):

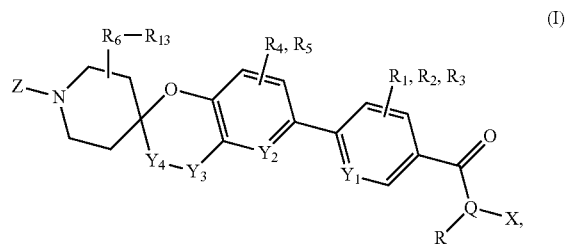

or a pharmaceutically acceptable salt thereof, wherein:
$Y_1$ is —$CR_{14}$— or N,
$Y_2$ is —$CR_{15}$— or N,
$Y_3$ is —C(O)—,
$Y_4$ is —$CH_2$—, or —$N(R_{16})$—,
or $Y_3$ and $Y_4$ together are —$C(R_{17})$=$C(R_{18})$—,
X is aryl, heteroaryl, arylalkyl, heteroarylalkyl, or amide,
Z is $C_2$ or greater alkyl or alkoxylalkyl,
R is H or $C_1$-$C_6$ alkyl,
$R_1$-$R_{18}$ are independently —H or $C_1$-$C_6$ alkyl, and
Q is CH or N; provided that when Q is N and R is H, X is not

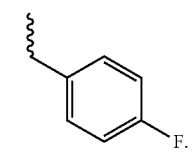

2. The compound of claim 1, wherein X is phenyl or substituted phenyl.
3. The compound of claim 2, wherein X is fluorophenyl.
4. The compound of claim 1, wherein R is H.
5. The compound of claim 1, wherein X is pyridinyl, substituted pyridinyl, isoxazolyl, or substituted isoxazolyl.
6. The compound of claim 5, wherein X is methylisoxazolyl, fluoropyridinyl or methylpyridinyl.
7. The compound of claim 1, wherein $Y_1$ is CH.
8. The compound of claim 1, wherein $Y_1$ is N.
9. The compound of claim 1, wherein $Y_2$ is CH.
10. The compound of claim 1, wherein $Y_2$ is N.
11. The compound of claim 1, wherein $Y_4$ is —$CH_2$—.
12. The compound of claim 11, wherein $Y_3$ and $Y_4$ together are —$C(R_{17})$=$C(R_{18})$—.
13. The compound of claim 1, wherein $Y_3$ and $Y_4$ together are —$C(R_{17})$=$C(R_{18})$—.
14. The compound of claim 1, wherein Z is $C_2$-$C_4$ alkyl.
15. The compound of claim 1, wherein Z is propyl.
16. The compound of claim 15, wherein Z is isopropyl.
17. The compound of claim 1, wherein Z is alkoxyalkyl.
18. The compound of claim 1, wherein Z is cyclobutylmethyl.
19. The compound of claim 1, wherein $R_1$-$R_{18}$ are each —H.
20. The compound of claim 1, wherein $R_{17}$ and $R_{18}$ are each —H.

21. A compound having the following formula:

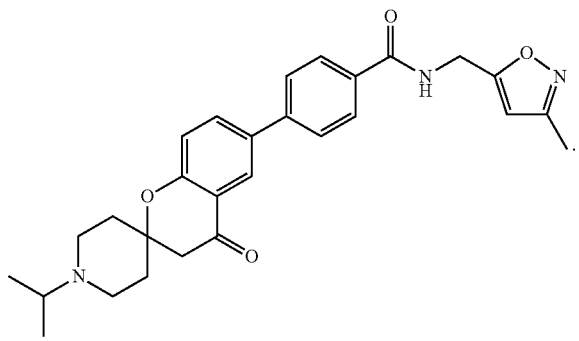 [SMILES: Cc1cc(CNC(=O)c2ccc(-c3ccc4c(c3)C(=O)CC3(CCN(C(C)C)CC3)O4)cc2)on1]

22. A compound having the following formula:

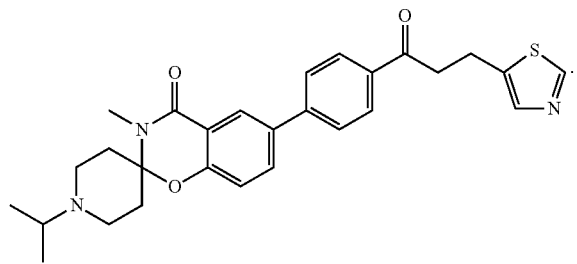 [SMILES: CC(C)N1CCC2(CC1)Oc1ccc(-c3ccc(C(=O)CCc4cncs4)cc3)cc1C(=O)N2C]

23. A method of inhibition of activated and/or proliferating B cells for therapeutic modulation of immunological disease, comprising administering to a patient in need thereof a composition comprising the compound of claim 1.

24. The method of claim 23, wherein the immunological disease is lupus, rheumatoid arthritis, scleroderma, psoriasis, Sjogren's syndrome, type I diabetes or multiple sclerosis.

25. A method of inducing, modulating or maintaining immunosuppression for transplant, comprising administering to a patient in need thereof a composition comprising the compound of claim 1.

26. A method of suppressing or modulating an immune response to a therapeutic biologic, comprising administering to a patient in need thereof a composition comprising the compound of claim 1.

27. The method of claim 26, wherein the therapeutic biologic is a recombinant protein, a nucleic acid, an antibody or a peptide.

28. A method of inhibiting tumor cell growth, wherein the tumor cells are NAPRT deficient, comprising administering to a patient in need thereof a composition comprising the compound of claim 1.

29. A method of treating leukemia and lymphoma, comprising administering to a patient in need thereof a composition comprising the compound of claim 1.

30. The method of claim 29, wherein the leukemia is acute lymphocytic leukemia.

31. A method of treating a NAD-requiring viral infection, comprising administering to a patient in need thereof a composition comprising the compound of claim 1.

32. The method of claim 31, wherein the viral infection is selected from influenza, RSV, HSV, HCV, HBV, HPV, HIV, CMV, EBOV, or EBV.

33. A method of inhibiting B cell differentiation into plasma cells, comprising contacting the B cells with the compound of claim 1.

34. A method of determining the presence of the compound of claim 1 in a sample, comprising contacting the sample with a binding agent that binds to the compound and detecting binding of the agent to the compound.

35. A compound of Formula (I):

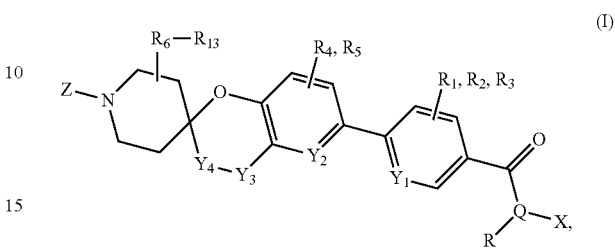

or a pharmaceutically acceptable salt thereof,
wherein:
$Y_1$ is —$CR_{14}$— or N,
$Y_2$ is $CR_{15}$ or N,
$Y_3$ is —C(O)—,
$Y_4$ is —$CH_2$, or —$N(R_{16})$—,
or $Y_3$ and $Y_4$ together are —$C(R_{17})$=$C(R_{18})$—,
X is aryl, heteroaryl, arylalkyl, heteroarylalkyl, or amide,
Z is $C_2$ or greater alkyl or alkoxylalkyl,
R is H or $C_1$-$C_6$ alkyl,
$R_1$-$R_{18}$ are independently —H or $C_1$-$C_6$ alkyl,
Q is CH or N; provided that when Q is N and R is H, X is not

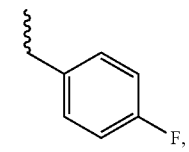

and
at least one atom in Formula (I) is replaced with a radioactive isotope or at least one group in Formula (I) is replaced with a fluorescent group.

36. A pharmaceutical composition, comprising the compound of claim 1 and a pharmaceutically acceptable carrier.

37. The compound of claim 1, wherein X is heteroarylalkyl.

38. A compound selected from the group consisting of:

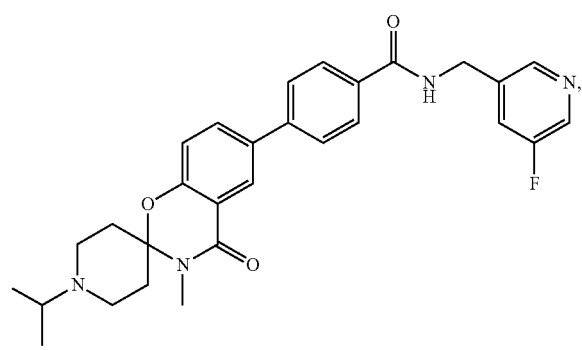

43
-continued
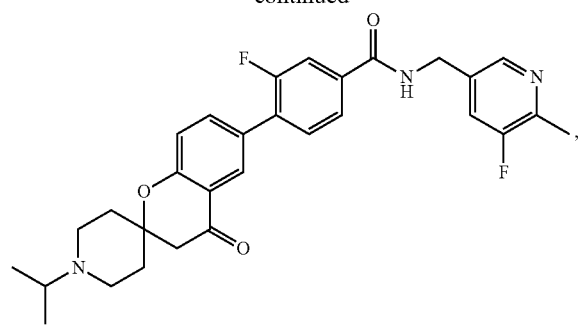
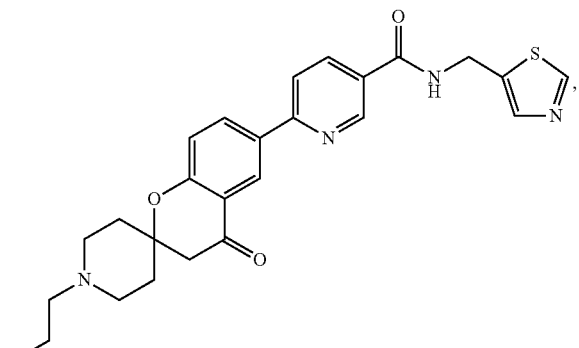
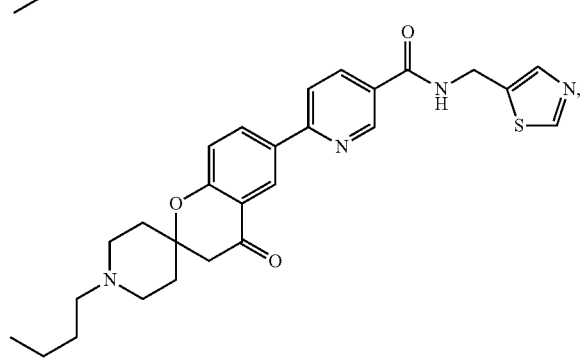
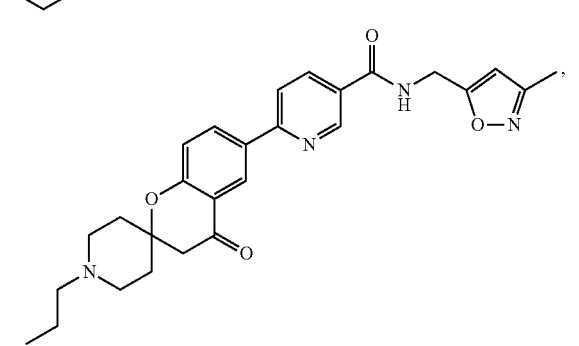
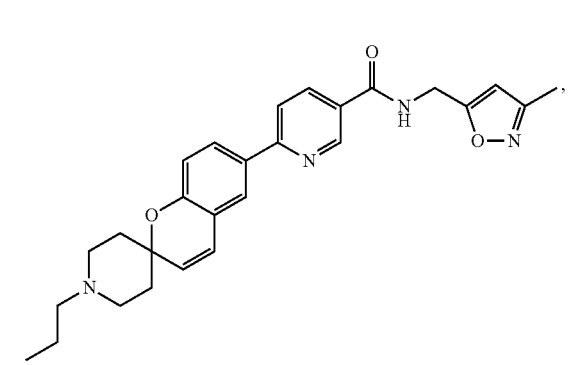
44
-continued
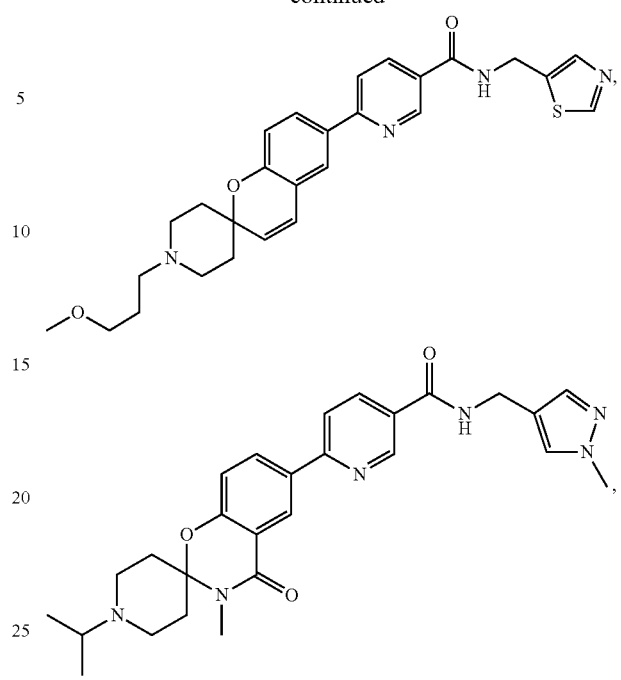
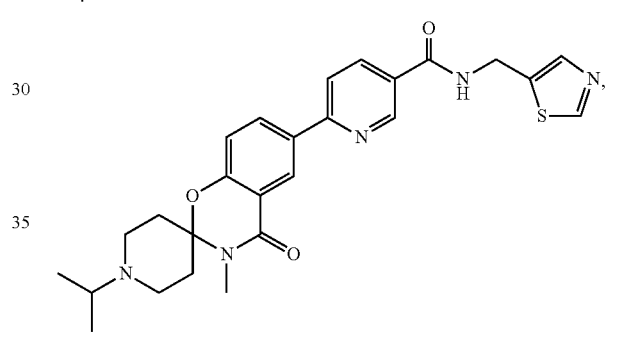
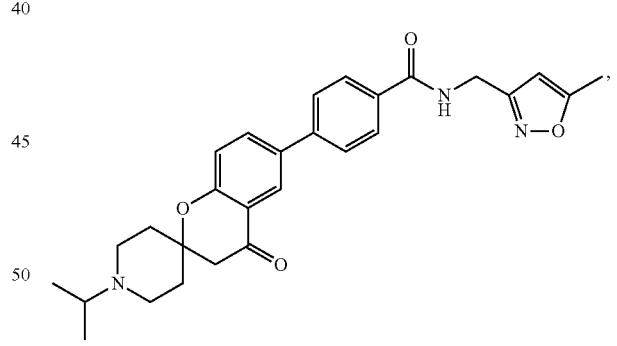
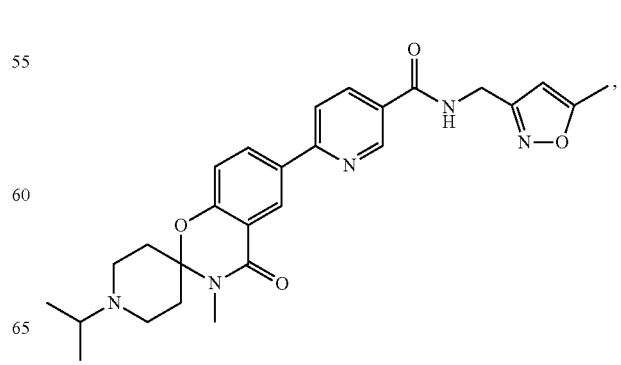

45
-continued
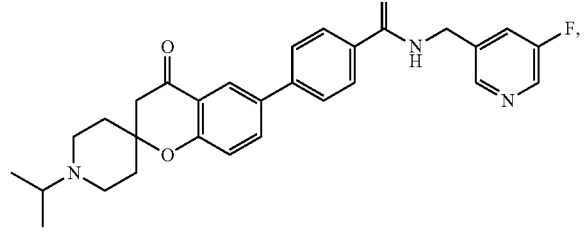
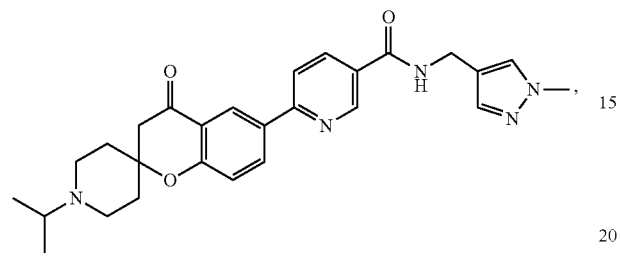
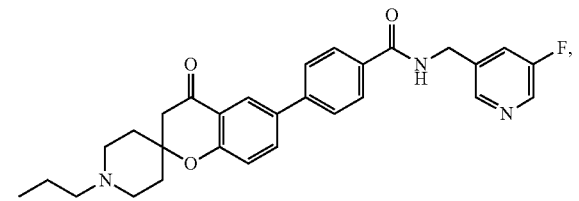
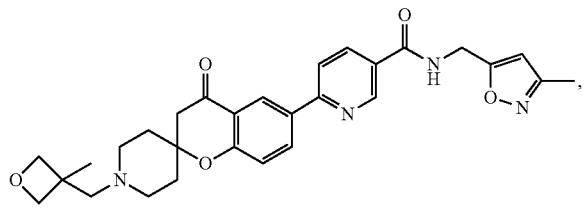
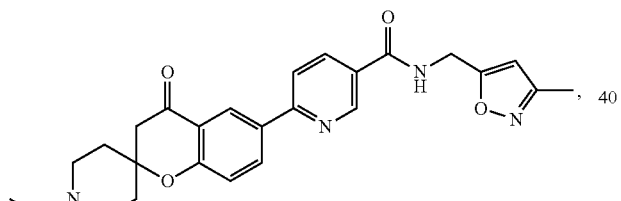
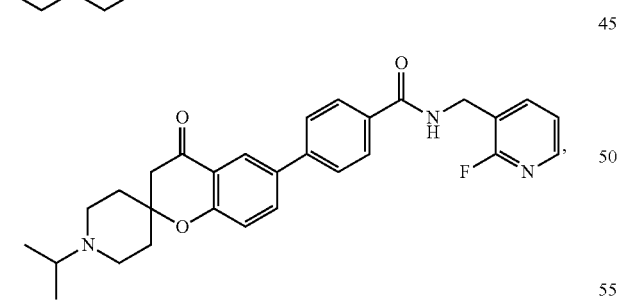
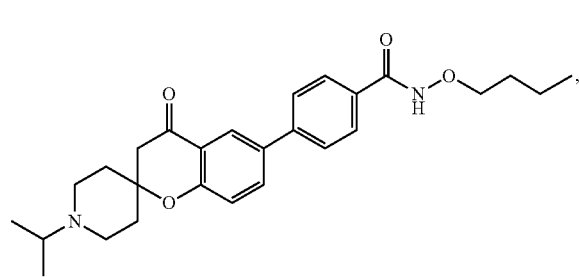
46
-continued
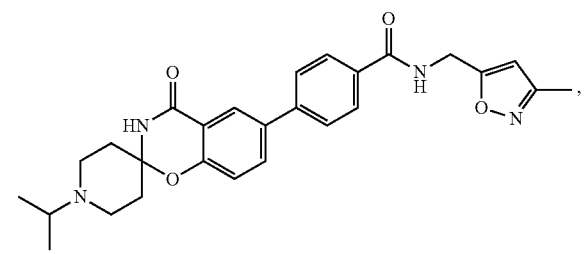
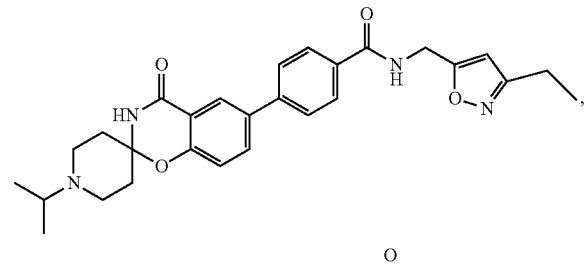
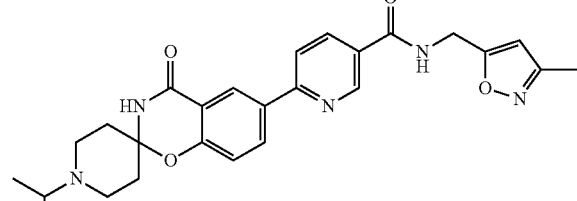
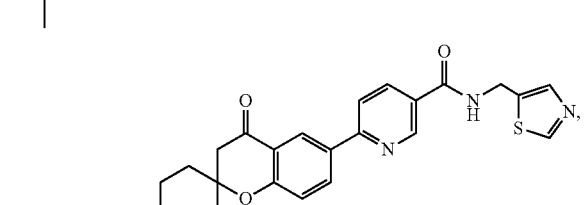
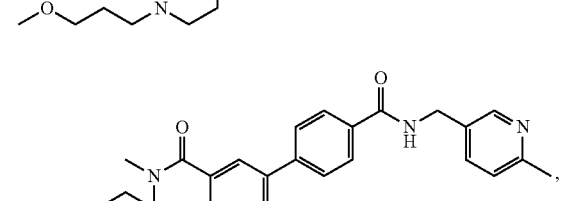
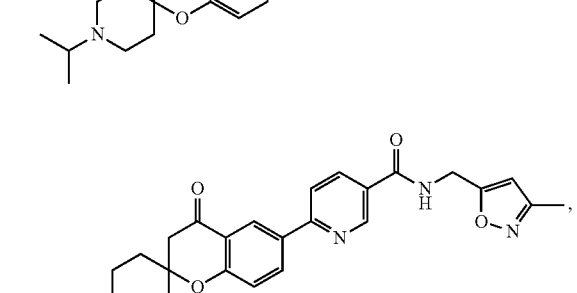
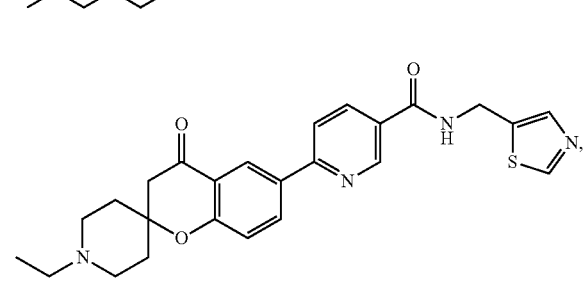

47
-continued
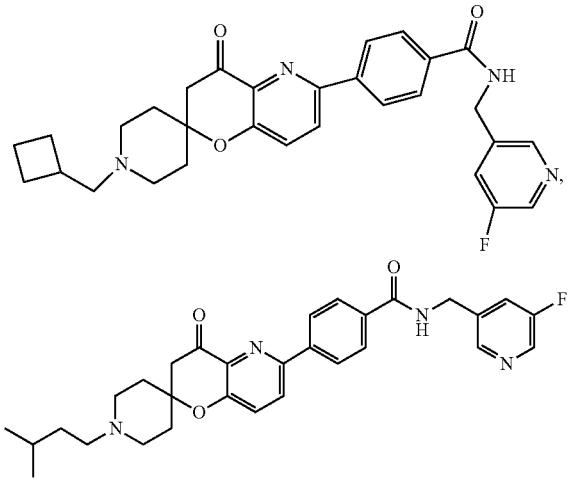
48
-continued
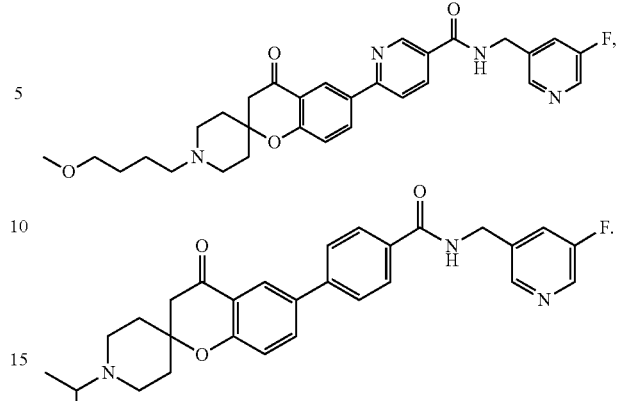
* * * * *

UNITED STATES PATENT AND TRADEMARK OFFICE
CERTIFICATE OF CORRECTION

PATENT NO. : 10,017,523 B2
APPLICATION NO. : 15/312482
DATED : July 10, 2018
INVENTOR(S) : Paul Mason et al.

It is certified that error appears in the above-identified patent and that said Letters Patent is hereby corrected as shown below:

In the Specification

Column 1, Line 18: Delete "phoshophoribosyltransferase" and insert -- phosphoribosyltransferase -- therefor.

Column 2, Line 4: Delete "-C(O)=;" and insert -- -C(O)-; -- therefor.

Column 2, Line 15: Delete " 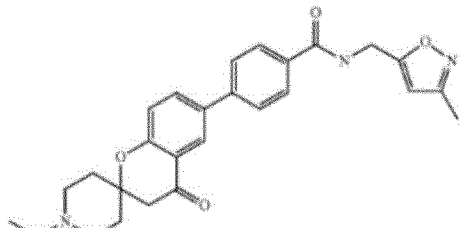 " and insert

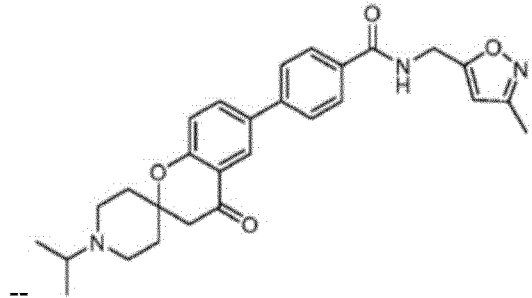

-- -- therefor.

Column 6, Line 40: After "oxadiazolyl" insert -- . --.

Column 6, Line 44: After "pyridazinyl" insert -- . --.

Signed and Sealed this
Twenty-fifth Day of September, 2018

Andrei Iancu
*Director of the United States Patent and Trademark Office*

Column 9, Line 15: Delete "azidodicarboxylate);" and insert -- azodicarboxylate); -- therefor.
Column 11, Line 50: Delete " 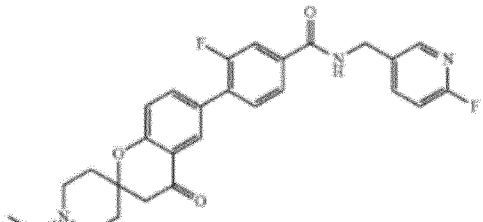 " and insert
" 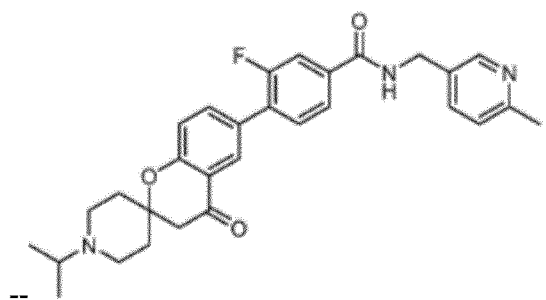 -- therefor.
Column 12, Line 25: Delete "idopropane" and insert -- iodopropane -- therefor.
Column 12, Line 45: Delete " 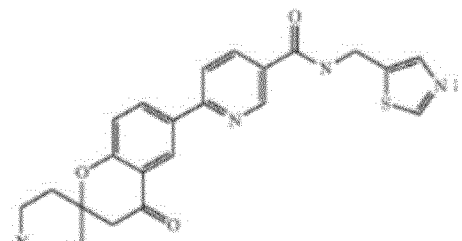 " and insert
-- 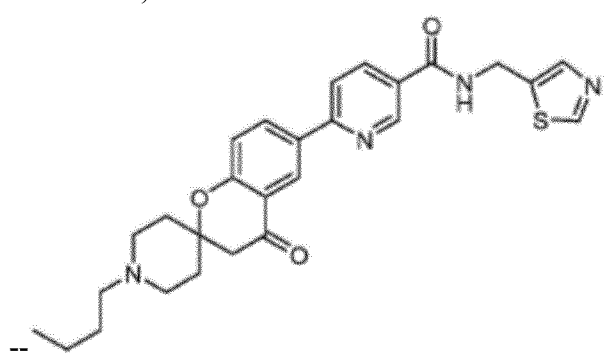 -- therefor.

CERTIFICATE OF CORRECTION (continued)
U.S. Pat. No. 10,017,523 B2

Page 3 of 6

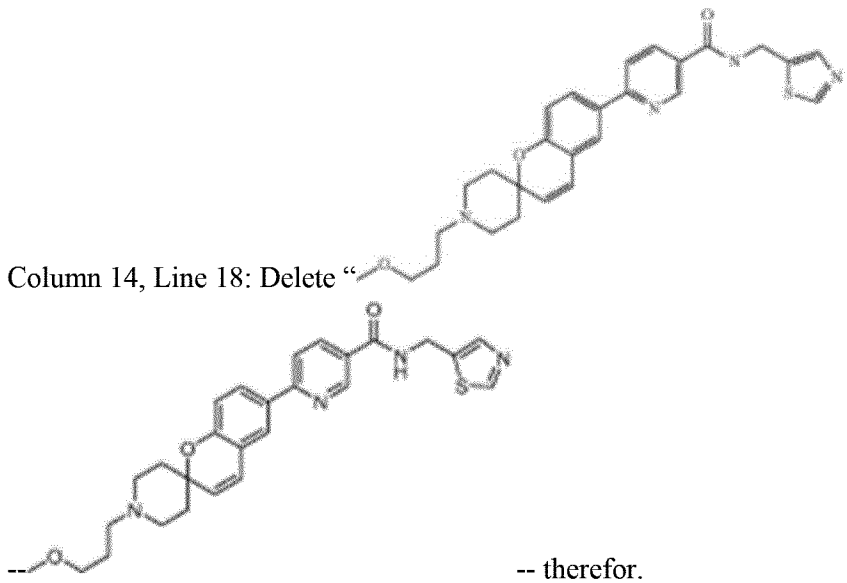

Column 14, Line 18: Delete " " and insert -- -- therefor.

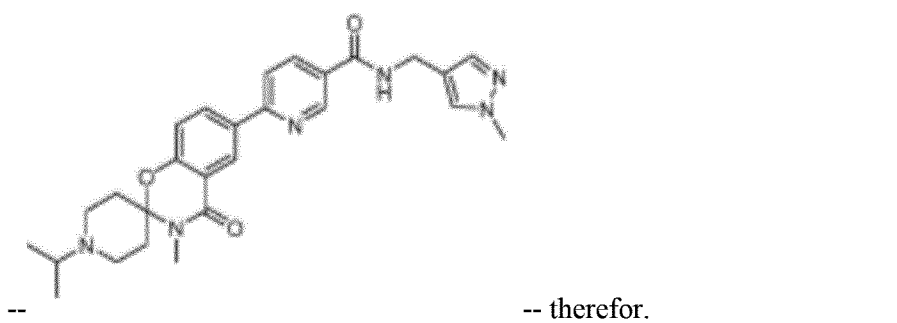

Column 14, Line 45: Delete " " and insert -- -- therefor.

Column 15, Line 6: Delete " " and insert

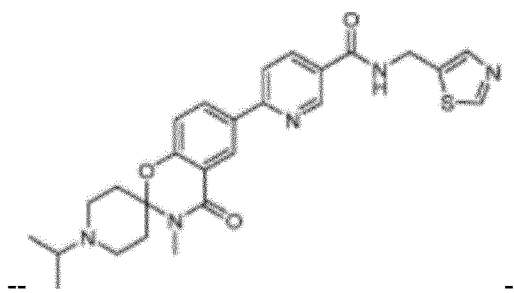 -- therefor.
Column 15, Line 32: Delete " 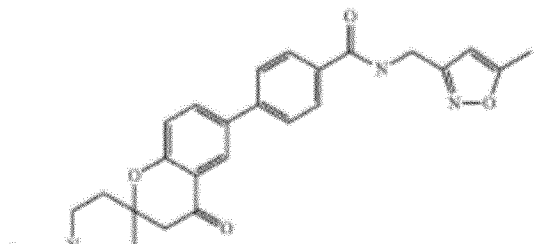 " and insert
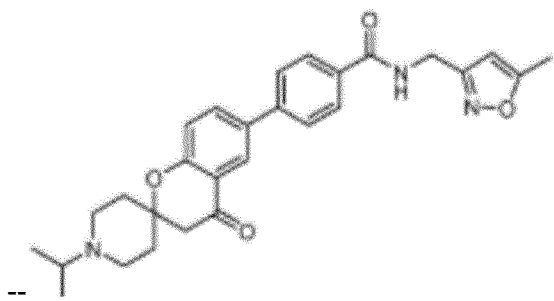 -- therefor.
Column 16, Line 15: Delete " 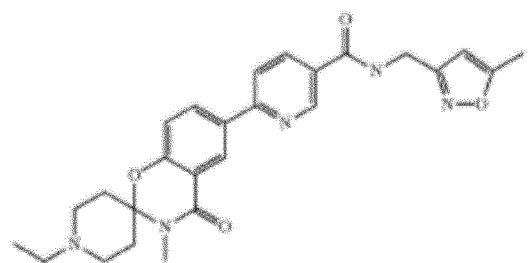 " and insert
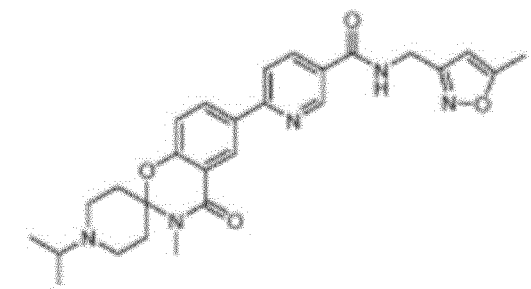 -- therefor.
Column 29, Line 60, Table 3: Delete "methy" and insert -- methyl -- therefor.

CERTIFICATE OF CORRECTION (continued)
U.S. Pat. No. 10,017,523 B2

Column 31, Line 54: Delete "EC$_{SO}$" and insert -- EC$_{50}$ -- therefor.

Column 31, Line 66: Delete "EC$_{SO}$" and insert -- EC$_{50}$ -- therefor.

Column 37, Line 35: Delete "sy 5 stemic" and insert -- systemic -- therefor.

In the Claims

Column 43, Line 2, Claim 38: Delete " 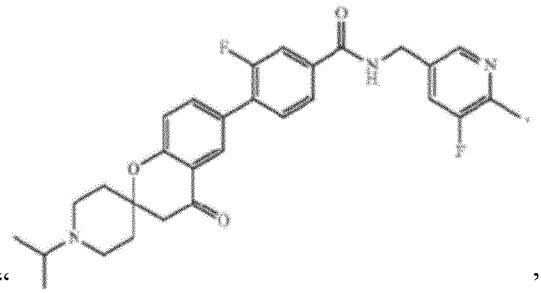 " and insert

-- 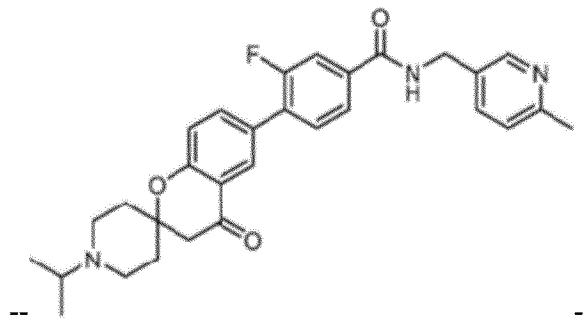 -- therefor.

Column 43, Line 40, Claim 38: Delete " 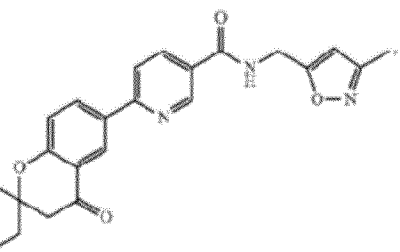 " and insert

-- 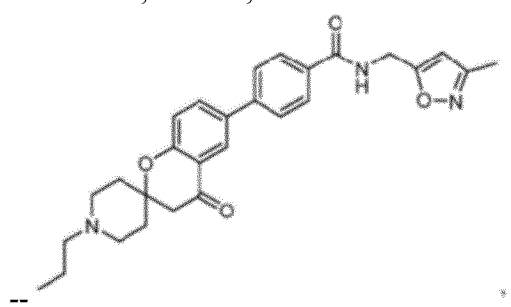 -- therefor.

CERTIFICATE OF CORRECTION (continued)
U.S. Pat. No. 10,017,523 B2

Column 45, Line 57, Claim 38: Delete " 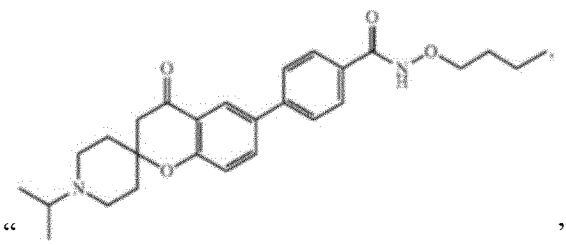 " and insert -- 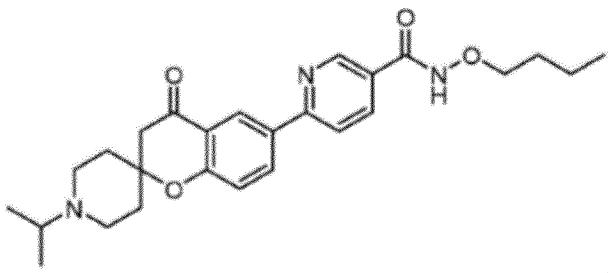 -- therefor.

Column 46, Line 13, Claim 38: Delete " 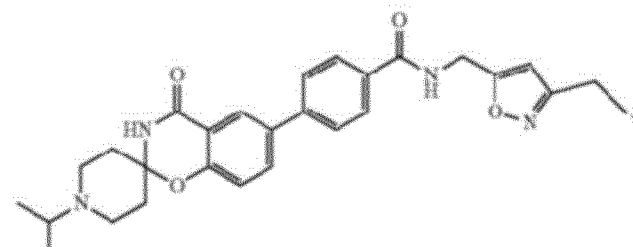 " and insert -- 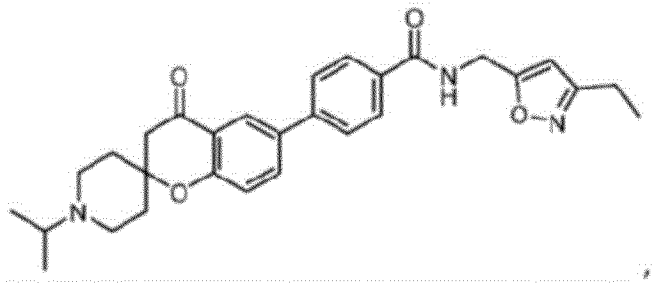 -- therefor.